(12) United States Patent
Danenberg (10) Patent No.: US 7,132,238 B2
(45) Date of Patent: *Nov. 7, 2006

(54) METHOD OF DETERMINING A CHEMOTHERAPEUTIC REGIMEN BASED ON ERCC1 EXPRESSION

(75) Inventor: Kathleen D. Danenberg, Altadena, CA (US)

(73) Assignee: Response Genetics, Inc., Los Angeles, CA (US)

( * ) Notice: Subject to any disclaimer, the term of this patent is extended or adjusted under 35 U.S.C. 154(b) by 487 days.

This patent is subject to a terminal disclaimer.

(21) Appl. No.: 10/453,784

(22) Filed: Jun. 4, 2003

(65) Prior Publication Data

US 2004/0005621 A1 Jan. 8, 2004

Related U.S. Application Data

(63) Continuation of application No. 09/988,784, filed on Nov. 20, 2001, now Pat. No. 6,602,670, which is a continuation-in-part of application No. 09/877,095, filed on Jun. 6, 2001, now Pat. No. 6,573,052, which is a continuation-in-part of application No. 09/796,491, filed on Mar. 2, 2001, now Pat. No. 6,518,416.

(60) Provisional application No. 60/250,470, filed on Dec. 4, 2000, provisional application No. 60/250,121, filed on Dec. 1, 2000.

(51) Int. Cl.
*C12Q 1/68* (2006.01)
*C12P 19/34* (2006.01)
*C07H 21/02* (2006.01)

(52) U.S. Cl. ............ 435/6; 435/91.1; 435/91.2; 435/91.21; 536/23.1; 536/23.5; 536/24.3; 536/24.33

(58) Field of Classification Search ............ None
See application file for complete search history.

(56) References Cited

U.S. PATENT DOCUMENTS

| | | | |
|---|---|---|---|
| 4,830,969 A | 5/1989 | Holmes | 435/259 |
| 4,843,155 A | 6/1989 | Chomczynski | 536/27 |
| 5,128,247 A | 7/1992 | Koller | 435/91 |
| 5,284,940 A | 2/1994 | Lin et al. | 536/25.4 |
| 5,346,994 A | 9/1994 | Chomczynski | 530/419 |
| 5,502,166 A | 3/1996 | Mishina | 530/350 |
| 5,620,852 A | 4/1997 | Lin et al. | 435/6 |
| 5,637,687 A | 6/1997 | Wiggins | 536/25.4 |
| 5,643,767 A | 7/1997 | Fischetti et al. | 435/91.3 |
| 5,654,179 A | 8/1997 | Lin | 435/91.2 |
| 5,672,696 A | 9/1997 | Wang et al. | 536/25.42 |
| 5,705,336 A * | 1/1998 | Reed et al. | 435/6 |
| 5,707,802 A | 1/1998 | Sandhu et al. | 435/6 |
| 5,728,822 A | 3/1998 | Macfarlane | 536/25.41 |
| 5,777,099 A | 7/1998 | Mehra | 536/25.42 |
| 5,945,515 A | 8/1999 | Chomczynski | 530/412 |
| 5,952,202 A | 9/1999 | Aoyagi et al. | |
| 5,989,857 A | 11/1999 | Mundschenk | 435/69.1 |
| 5,994,076 A | 11/1999 | Chenchik et al. | 435/6 |
| 6,010,700 A | 1/2000 | Richt | 424/186.1 |
| 6,043,354 A | 3/2000 | Hillebrand et al. | 536/25.42 |
| 6,204,375 B1 | 3/2001 | Lader | 536/25.4 |
| 6,207,408 B1 | 3/2001 | Essenfeld et al. | 435/40.5 |
| 6,248,535 B1 * | 6/2001 | Danenberg et al. | 435/6 |
| 6,602,670 B1 * | 8/2003 | Danenberg | 435/6 |

FOREIGN PATENT DOCUMENTS

| | | |
|---|---|---|
| WO | WO 95/28489 A | 10/1995 |
| WO | WO 97/05248 | 2/1997 |
| WO | WO 97/35034 | 9/1997 |
| WO | WO 98/41648 | 9/1998 |

OTHER PUBLICATIONS

Reed, E. Cancer Treatment Reviews (1998) 24: 331-344.*
I.Miiyauchi, et al., "Further study of hepatitis C virus RNA detection in formalin -fixed, paraffin -embedded liver tissues by ligation -dependent polymerase chain reaction" Pathology International 1998:48: 428-432.
G. Stanta, et al., *RNA Quantitative Analysis from Fixed and Paraffin-Embedded Tissues*, Methods in Molecular Biology (1998) vol. 86, pp. 113-119.
G. Stanta, et al., *RNA Extraction from Formalin-Fixed and Paraffin-Embedded Tissues*, Methods in Molecular Biology (1998) vol. 86, pp. 23-26.
Ardalan, B., et al., "Thymidylate Synthase Gene Expression in Normal and Malignant Colorectal Tissues: Relation to in vivo Response and Survival," Proceedings of the American Association for Cancer Research, vol. 37, Abstract No. 1376 (Mar. 1996).
Ausubel, F.M., ed., *Current Protocols In Molecular Biology*, John Wiley & Sons, Inc., vol. 1.; Strauss, W. M., "Preparation of Genomic DNA from Mammalian Tissue," Unit 2.2, pp. 2.2.1-2.2.3 (1998).
Ausubel, F.M., ed., *Current Protocols In Molecular Biology*, John Wiley & Sons, Inc., vol. 1.; Richards, E., et al., "Preparation of Genomic DNA from Plant Tissue," Unit 2.3, pp. 2.3.1-2.3.7 (1994).

(Continued)

*Primary Examiner*—Kenneth R. Horlick
*Assistant Examiner*—Christopher M. Babic
(74) *Attorney, Agent, or Firm*—Kenyon & Kenyon LLP (57) ABSTRACT

The present invention relates to prognostic methods which are useful in medicine, particularly cancer chemotherapy. The object of the invention is to provide a method for assessing ERCC1 expression levels in fixed or fixed and paraffin embedded tissues and determine a platinum-based chemotherapy by examination of the amount of ERCC1 mRNA in a patient's tumor cells and comparing it to a predetermined threshold expression level. More specifically, the invention provides to oligonucleotide primer pair ERCC1 and methods comprising their use for detecting levels of ERCC1 mRNA.

4 Claims, 4 Drawing Sheets

OTHER PUBLICATIONS

Ausubel, F.M., ed., *Current Protocols In Molecular Biology*, John Wiley & Sons, Inc., vol. 1.;Wilson, K., "*Preparation of Genomic DNA from Bacteria*," Unit 2.4, pp. 2.4.1-2.4.5 (1994).

Banerjee, S.K., et al, "*Microwave-Based DNA Extraction from Paraffin-Embedded Tissue for PCR Amplification*," BioTechniques, vol. 18, No. 5, pp. 768, 770, 772, 773 (1995).

Benhattar, J., et al., "*p53 Mutations as a Possible Predictor of Response to Chemotherapy in Metastatic Colorectal Carcinomas*," Int. J. Cancer (Pred. Oncol.), vol. 69, pp. 190-192 (1996).

Bresters, D., et al., "*Detection of Hepatitis C Viral RNA Sequences in Fresh and Paraffin-Embedded Liver Biopsy Specimens of Non-A, Non-B Hepatitis Patients*," J. Hepat., vol. 15, pp. 391-395 (1992).

Bresters, D., et al., "*The Duration of Fixation Influences the Yield of HCV cDNA-PCR Products from Formalin-Fixed, Paraffin-Embedded Liver Tissues*," J. Virol. Method, vol. 48, pp. 267-272 (1994).

Chirgwin, J., M., et al., "*Isolation of Biologically Active Ribonucleic Acid from Sources Enriched in Ribonuclease,*" Biochemistry, vol. 18, No. 24, pp. 5294-5299 (1979).

Chomczynski, P., et al., "*Single-Step Method of RNA Isolation by Acid Guanidinium Thiocyanate-Phenol-Chloroform Extraction*," Analytical Biochemistry, vol. 162, pp. 156-159 (1987).

Chomczynski, P., "*A Reagent for the Single-Step Simultaneous Isolation of RNA, DNA and Proteins from Cell and Tissue Samples*," BioTechniques, vol. 15, No. 3, pp. 532-534, 536-537 (1993).

Coombs, N. J., et al., "*Opimisation of DNA and RNA Extraction from Archival Formalin-Fixed Tissue*," Nucl. Acids Research, vol. 27, No. 16, pp. i-iii (1999).

Dakhama, A., et al., "*Amplification of Human β-Actin Gene by the Reverse Transcripase-Polymerase Chain Reaction: Implications for Assessment of RNA from Formalin-Fixed, Paraffin-Embedded Material*," J. Histochem. and Cytochem., vol. 44, No. 10, pp. 1205-1207 (1996).

de Andrés, B., et al., "*Improved Method for mRNA Extraction from Paraffin-Embedded Tissues*," BioTechniques, vol. 18, No. 1, pp. 42-43 (1995).

Eads, C. A., et al., "*CpG Island Hypermethylation in Human Colorectal Tumors is Not Associated with DNA Methyltransferase Overexpression*," Cancer Research, vol. 59, pp. 2302-2306 (1999).

Edamoto, Y., et al., "*Hepatitis C and B Virus Infections in Hepatocellular Carcinoma*," CANCER, vol. 77, No. 9, pp. 1787-1791 (1996).

Farrugia, D., et al., "*A pharmacodynamic (PD) study of the thymidylate, synthase (TS) Inhibitor Tomudex™ in advanced colorectal cancer (CRC)*," Proceedings of the American Association for Cancer Research, Eighty-eighth Annual Meeting (Apr. 12-16, 1997), vol. 38, Abstract #4132.

Finke, J., et al., "*An Improved Strategy and a Useful Housekeeping Gene for RNA Analysis from Formalin-Fixed, Paraffin-Embedded Tissues by PCR*," BioTechniques, vol. 14, No. 3, pp. 448-453 (1993).

Goldsworthy, S. M., et al., "*Effects of Fixation on RNA Extraction and Amplification from Laser Capture Microdissected Tissue*," Molecular Carcinogenesis, vol. 25, pp. 86-91 (1999).

Greer, C. E., et al., "*PCR Amplification from Paraffin-Embedded Tissues*," Am. J. Clin. Pathol., vol. No. 95, No. 2, pp. 117-124 (1991).

Gruber, A. D., et al., "*Detection of Bovine Viral Diarrhea Virus RNA in Formalin-Fixed, Paraffin-Embedded Brain Tissue by Nested Polymerase Chain Reaction*," J. Virol. Methods, vol. 43, pp. 309-319 (1993).

Guerrero, R.B., et al., "*Effects of Formalin Fixation and Prolonged Block Storage on Detection of Hepatitis C Virus RNA in Liver Tissue*," Diag. Molec. Path., vol. 6, No. 5, pp. 277-281 (1997).

Hodges, E., et al., "*Isolation of Nucleic Acid from Paraffin Embedded Tissue for PCR Amplification and Sequencing of TcR Vβ Genes*," Leuk. Research, vol. 19, No. 3, pp. 183-186 (1995).

Horie, N., et al., "*Functional Analysis and DNA Polymorphism of the Tandemly Repeated Sequences in the 5' terminal Regulatory Region of the Human Gene for Thymidylate Synthase*," Cell Structure and Function, vol. 20, No. 3, pp. 191-197 (1995).

Horikoshi, T., et al., "*Quantitation of Thymidylate Synthase, Dihydrofolate Reductase, and DT-Diaphorase Gene Expression in Human Tumors using the Polymerase Chain Reaction*," Cancer Res., vol. 52, pp. 108-116 (1992).

Hsuih, T. C. H., et al., "*Novel, Ligation-Dependent PCR Assay for Detection of Hepatitis C Virus in Serum*," J. Clin. Micorbiol., vol. 34, No. 3, pp. 501-507 (1996).

Ichikawa, W., et al., "*Expression of Dihydropyrimidine Dehydrogenase (DPD) and Thymidylate Synthase (TS) mRNA in Primary Tumor Predicts the Anti-Tumor Effect in 5-Fluorouracil (FU Based Chemotherapy for Gastrointestinal (GI) Cancer*," Proceedings of the American Association for Cancer Research, vol. 42, Abstract No. 3326 (Mar. 2001).

Iwamoto, K. S., et al., "*Feasibility of Using Decades-Old Archival Tissues in Molecular Oncology/Epidmiology*," Am. J. Path., vol. 149, No. 2, pp. 399-406 (1996).

Jackman, A. L., et al., "*Thymidylate Synthetase Inhibitors: Experimental and Clinical Aspects*," Chapter 7 in Experimental and Clinical Progress in Cancer Chemotherapy, F.M. Muggia, ed., Martinus Nijhoff, Boston (1985), pp. 155-210.

Jiang, Y.-H., et al., "*A Rapid RT-PCR Method for Detection of Intact RNA in Formalin-Fixed Paraffin-Embedded Tissues*," Nucl. Acids. Res., vol. 23, No. 15, pp. 3071-3072 (1995).

Kawakami, K., et al., "*Polymorphic Tandem Repeats in the Thymidylate Synthase Gene is Associated with its Protein Expression in Human Gastrointestinal Cancers*," Proceedings of the American Society of Clinical Oncology, vol. 17, Abstract No. 1128 (May 1998).

Keyomarsi, K., et al., "*Mechanism of the Cytotoxic Synergism of Fluoropyrimidines and Folinic Acid in Mouse Leukemic Cells*," J. Biol. Chem., vol. 263, No. 28, pp. 14402-14409 (1988).

Kiyosawa, K., et al., "*Interrelationship of Blood Transfusion, Non-A, Non-B Hepatitis and Hepatocellular Carcinoma: Analysis by Detection of Antibody to Hepatitis C Virus*," Hepatology, vol. 12, No. 4, pp. 671-675 (1990).

Koopmans, M., et al., "*Optimization of Extraction and PCR Amplification of RNA Extracts from Paraffin-Embedded Tissue in Different Fixatives*," J. Virological Methods, vol. 43, pp. 189-204 (1993).

Leichman, C. G., et al., "*Quantitation of Intratumoral Thymidylate Synthase Expression Predicts for Disseminated Colorectal Cancer Response and Resistance to Protracted-Infusion Fluorouracil and Weekly Leucovorin*," J. Clinical Oncology, vol. 15, No. 10, pp. 3223-3229 (1997).

Lenz, H.-J., et al., "*p53 and Thymidylate Synthase Expression in Untreated Stage II Colon Cancer: Associations with Recurrence, Survival, and Site*," Clinical Cancer Research, vol. 4, pp. 1227-1234 (1998).

Lenz, H.-J., et al., "*Thymidylate Synthase mRNA Level in Adenocarcinoma of the Stomach: A Predictor for Primary Tumor Response and Overall Survival*," J. Clinical Oncology, vol. 14, No. 1, pp. 176-182 (1996).

Macfarlane, D. E., et al., "*Introduction to Isolating RNA*," in RNA Isolation and Characterization Protocols, R. Rapley and D. L. Manning, eds., Humana Press (Series: Methods in Molecular Biology™), Totowa, N. J. (1998), pp. 1-6.

Marsh, S., et al., "*Ethnic Variation in the Thymidylate Synthase Enhancer Region Polymorphism among Caucasian and Asian Populations*," Genomics, vol. 58, pp. 310-312 (1999).

Mies, C., "*A Simple, Rapid Method for Isolating RNA from Paraffin-embedded Tissues for Reverse Transcription-Polymerase Chain Reaction (RT-PCR)*," J. Histochemistry and Cytochemistry, vol. 42, No. 6, pp. 811-813 (1994).

Mizuno, T., et al., "*RNA from Decades-Old Archival Tissue Blocks for Retrospective Studies*," Diagnostic Molecular Pathology, vol. 7, No. 4, pp. 202-208 (1998).

Mukhopadhyay, T., et al., "*Isolation of Total RNA from Tissues or Cell Lines*," in RNA Isolation and Charcaterization Protocols, R. Rapley and D. L. Manning, eds., Humana Press (Series: Methods in Molecular Biology™), Totowa, N.J. (1998), pp. 55-59.

Park, Y. N., et al., "*Detection of Hepatitis C Virus RNA Using Ligation-Dependent Polymerase Chain Reaction in Formalin-Fixed, Paraffin-Embedded Liver Tissues*," American Journal of Pathology, vol. 149, No. 5, pp. 1485-1491 (1996).

Rupp, G. M., et al., "*Purification and Analysis of RNA from Paraffin-Embedded Tissues*," BioTechniques, vol. 6, No. 1, pp. 56-60 (1988).

Sambrook, J., et al., "*Isolation of High-Molecular-Weight DNA from Mammalian Cells*," in Molecular Cloning: A Laboratory Manual, 2$^{nd}$ Ed., Cold Spring Harbor Laboratory Press (1989), pp. 9.14-9.23.

Sander, C. A., et al., "*p53 Mutation is Associated with Progression in Follicular Lymphomas,*" Blood, vol. 82, No. 7, pp. 1994-2004 (1993).

Santos, A. C., et al., "*Simultaneous Extraction of RNA and DNA from Paraffin-Embedded Tissues,*" Trends in Genetics, vol. 9, No. 7, p. 231 (1993).

Soguero, C., et al., "*Detection of Hepatitis C Virus RNA in More Than 20-Year Old Paraffin-Embedded Liver Tissue,*" Laboratory Investigation, vol. 79, No. 3, pp. 365-366 (1999).

Sorg, I., et al., "*Detection of Borna Disease Virus RNA in Formalin-Fixed, Paraffin-Embedded Brain Tissues by Nested PCR,*" J. Clinical Microbiology, vol. 33, No. 4, pp. 821-823 (1995).

Spears, C. P., et al., "*In Vivo Kinetics of Thymidylate Synthetase Inhibition in 5-Fluorouracil-Sensitive and -Resistant Murine Colon Adenocarcinomas,*" Cancer Research, vol. 42, pp. 450-456 (1982).

Stanta, G., et al., "*RNA Extracted from Paraffin-Embedded Human Tissues is Amenable to Analysis by PCR Amplification,*" BioTechniques, vol. 11, No. 3, pp. 304-308 (3 pages) (1991).

Swain, S. M., et al., "*Fluorouracil and High-Dose Leucovorin in Previously Treated Patients with Metastatic Breast Cancer,*" J. Clinical Oncology, vol. 7, No. 7, pp. 890-899 (1989).

Wei, X., et al., "*Molecular Basis of the Human Dihydropyrimidine Dehydrogenase Deficiency and 5-Fluorouracil Toxicity,*" J. Clinical Investigation, vol. 98, No. 3, pp. 610-615 (1996).

v. Weizsäcker, F., et al., "*A Simple and Rapid Method for the Detection of RNA in Formalin-Fixed, Paraffin-Embedded Tissues by PCR Amplification,*" Biochem. and Biophys. Research Comm., vol. 174, No. 1, pp. 176-180 (1991).

Iqbal S, Lenz HJ, "Determinants of prognosis and response to therapy in colorectal cancer,"Curr Oncol Rep. Mar. 2001;3(2):102-8.

Gilmore PM, et al., "The Development and Optimisation of a Quantitative RT-PCR Technique from Formalin-Fixed and Paraffin-Embedded (FFPE) Tissues, Using the Thymidylate Synthase (TS) Gene As a Target," American Society of Clinical Oncology: 17: Abstract 2159, 1998.

Salonga D, Danenberg KD, Johnson M, Metzger R, Groshen S, Tsao-Wei DD, Lenz HJ, Leichman CG, Leichman L, Diasio RB, Danenberg PV, "Colorectal tumors responding to 5-fluorouracil have low gene expression levels of dihydropyrimidine dehydrogenase, thymidylate synthase, and thymidine phosphorylase," Clin Cancer Res. Apr. 2000;6(4):1322-7.

Specht K, Richter T, Muller U, Walch A, Werner M, Hofler H, "Quantitative gene expression analysis in microdissected archival formalin-fixed and paraffin-fixed and paraffin-embedded tumor tissue," Am J Pathol. Feb. 2001;158(2):419-2.

Gibson, UE, "A novel method for real timequantitative RT-PCR," Genome Res 6: 995-1001, 1996.

Heid, CA, "Real Time quantitative PCR," Genome Res 6: 986-994, 1996.

Schena, Mark et al. "Quantitative Monitoring of Gene Expression Patterns With a Complementary DNA Microarray", Science (1995) vol. 270:467-470.

Zhao, Nanding et al., "High-Density cDNA Filter Analysis: A Novel Approach for Large-Scale, Quantitative Analysis of Gene Expression", Gene (1995) vol. 156: 207-213.

Dabholkar M, Thornton K, Vionnet J, Bostick-Bruton F, Yu JJ, Reed E, "Increased mRNA levels of xeroderma pigmentosum complementation group B (XPB) and Cockayne's syndrome complementation group B (CSB) without increased mRNA levels of multidrug-resistance gene (MDR1) or metallothionein-II (MT-II) in platinum-resistant human ovarian cancer tissues." Biochem Pharmacol. Dec. 1, 2000;60(11):1611-9.

Damia G, Guidi G, D'Incalci M, "Expression of genes involved in nucleotide excision repair and sensitivity to cisplatin and melphalan in human cancer cell lines," Eur J Cancer, Oct. 1998;34(11):1783-8.

Codegoni AM, Broggini M, Pitelli MR, Pantarotto M, Torri V, Mangioni C, D'Incalci M, "Expression of genes of potential importance in the response to chemotherapy and DNA repair in patients with ovarian cancer," Gynecol Oncol. Apr. 1997; 65(1):130-7.

Zhao R, Rabo YB, Egyhazi S, Andersson A, Edgren MR, Linder S, Hansson J., "Apoptosis and c-jun induction by cisplatin in a human melanoma cell line and a drug-resistant daughter cell line," Anticancer Drug, Oct. 1995;6(5):657-68.

Dabholkar M, Bostick-Bruton F, Weber C, Egwuagu C, Bohr VA, Reed E., "Expression of excision repair genes in non-malignant bone marrow from cancer patients," Mutat Res. Jan. 1993;293(2):151-60.

Dabholkar M, Bostick-Bruton F, Weber C, Bohr VA Egwuagu C, Reed E., "ERCC1 and ERCC2 expression in malignant tissues from ovarian cancer patients," J Natl Cancer Inst. Oct 7, 1992;84(19):1512-7.

Metzger R, et al., "ERCC1 mRNA Levels Complement Thymidylate Synthase mRNA Levels in predicting response and survival for gastric cancer patients receiving combination cisplatin and fluorouracil chemotherapy," J Clin Oncol 16: 309-316, 1998.

Taverna P, Hansson J, Scanlon KJ, Hill BT, "Gene expression in X-irradiated human tumour cell lines expressing cisplatin resistance and altered DNA repair capacity," Carcinogenesis. Sep. 1994;15(9):2053-6.

Dabholkar M, Vionnet J, Bostick-Bruton F, Yu JJ, Reed E. Messenger RNA levels of XPAC and ERCC1 in ovarian cancer tissue correlate with response to platinum-based chemotherapy. J Clin Invest. Aug. 1994;94(2):703-8.

Li Q, Yu JJ, Mu C, Yunmbam MK, Slavsky D, Cross CL, Bostick-Bruton F, Reed E. Association between the level of ERCC-1 expression and the repair of cisplatin-induced DNA damage in human ovarian cancer cells. Anticancer Res. Mar.-Apr. 2000;20(2A):645-52.

Johnston et al., TS Expression from Formalin Fixed Paraffin Embedded (FFPE) tissues using Quantitative RT-PCR correlates with frozen tissue data and predicts for response to 5-FU in metastatic colorectal cancers. American Society of Clinical Oncology: Astract 2383, 1999.

Aschele, C., et al., "*Thymidylate Synthase Protein Expression in Primary Colorectal Cancer Compared with the Corresponding Distant Metastases and Relationship with the Clinical Response to 5-Fluorouracil,*" Clinical Cancer Research, 6: 4797-4802 (2000).

Beck, A., et al., "*A Role for Dihydropyrimidine Dyhydrogenase and Thymidylate Synthase in Tumour Sensitivity to Fluorouracil,*" European Journal of Cancer, 30A(10):1517-1522 (1994).

Chen, Z., et al., "*Correlation of Cisplatin Sensitivity with Differential Alteration of EGFR Expression in Head and Neck Cancer Cells,*" Anticancer Research 20:899-902 (2000).

Etienne M.C., et al., "*Response to Fluorouracil Therapy in Cancer Patients: The Role of Tumoral Dihydropyrimidine Dehydrogenase Activity,*" Journal of Clinical Oncology, 13(7):1663-1670 (1995).

Gorlick R. et al., "*Higher Levels of Thymidylate Synthase Gene Expression Are Observed in Pulmonary as Compared With Hepatic Metastases of Colorectal Adenocarcinoma*", Journal of Clinical Oncology, 16(4):1465-1469 (1998).

Kornmann M., et al., "*Thymidylate synthase is a predictor for response and resistance in hepatic artery infusion chemotherapy,*" Cancer Letters, 118:29-35 (1997).

Lenz H.J., et al., "*P53 Point Mutations and Thymidylate Synthase Messenger RNA Levels in Disseminated Colorectal Cancer: An Analysis of Response and Survival,*" Clinical Cancer Research, 4:1243-1250 (1998).

Neskovic-Konstantinovic, Z., et al., "*Expression of Epidermal Growth Factor Receptor in Breast Cancer, from Early Stages to Advanced Disease,*" J. Exp. Clin. Cancer Res., 18(3):347-355 (1999).

Newby J.C., et al., "*Expression of Epidermal Growth Factor Receptor and c-erbB2 during the Development of Tamoxifen Resistance in Human Breast Cancer,*" Clinical Cancer Research, 3:1643-1651 (1997).

Nicholson, R.I., et al., "*Relationship Between EGF-R, c-erbB-2 Protein Expression and Ki67 Immunostaining in Breast Cancer and Hormone Sensitivity,*" Eur. J. Cancer, 29A(7):1018-1023 (1993).

Wong, NACS, et al., "*Nuclear thymidylate synthase expression, p53 expression and 5FU response in colorectal carcinoma,*" British Journal of Cancer, 85(12):1937-1943 (2001).

Yamada, H., et al., "*Thymidylate Synthase Gene Expression in Primary Colorectal Cancer and Metastatic Sites,*" Clinical Colorectal Cancer, 1(3):169-173 (2001); discussion p. 174.

\* cited by examiner

FIG. 1

CHART ILLUSTRATING HOW TO CALCULATE *ERCC1* EXPRESSION RELATIVE TO AN INTERNAL CONTROL GENE

| | Sample | from "test" reactions | | | | from "calibration" reactions | | | | Uncorrected Gene Expression (UGE) | Known *ERCC1* values | Derivation of $K_{ERCC1}$ (average K) | | Relative Corrected *ERCC1* exp. |
|---|---|---|---|---|---|---|---|---|---|---|---|---|---|---|
| | | $C_T$ *ERCC1* | $C_T$ β-actin | $\Delta C_T$ | $2^{-\Delta C_T}$ | $C_T$ *Calib.RNA* | $C_T$ β-actin | $\Delta C_T$ | $2^{-\Delta C_T}$ | $2^{-\Delta C_T}/2^{-\Delta C_T}$ | | K | $K_{ERCC1}$ | |
| Experimental | unknown1 | 26.68 | 21.17 | 7.51 | 0.00549 | - | - | - | - | 0.737 | - | | 1.54 $\times 10^{-3}$ | 1.13 $\times 10^{-3}$ |
| | unknown2 | 24.8 | 17.64 | 7.16 | 0.00699 | - | - | - | - | 0.9395 | - | | 1.54 $\times 10^{-3}$ | 1.45 $\times 10^{-3}$ |
| | Calib. RNA | - | - | - | - | 27.81 | 20.71 | 7.07 | 0.0074 | 0.0074/0.0074 = 1 | | | | |
| From Known Samples | AG221 | 34.46 | 28.56 | 5.9 | 0.167 | - | - | - | - | 2.81 | 4.32 $\times 10^{-3}$ | 1.54 $\times 10^{-3}$ | 1.54 $\times 10^{-3}$ | - |
| | AG222 | 33.93 | 27.21 | 6.72 | 0.0095 | - | - | - | - | 1.59 | 2.45 $\times 10^{-3}$ | 1.54 $\times 10^{-3}$ | 1.54 $\times 10^{-3}$ | - |
| | AG252 | 36.9 | 29.43 | 7.47 | 0.0056 | - | - | - | - | 0.946 | 1.46 $\times 10^{-3}$ | 1.54 $\times 10^{-3}$ | 1.54 $\times 10^{-3}$ | - |
| | Adult Lung | 25.2 | 17.3 | 8 | 0.0039 | - | - | - | - | 0.655 | 1.009 $\times 10^{-3}$ | 1.54 $\times 10^{-3}$ | 1.54 $\times 10^{-3}$ | - |
| | PC3 | 24.51 | 16.47 | 8.04 | 0.0038 | - | - | - | - | 0.637 | 0.981 $\times 10^{-3}$ | 1.54 $\times 10^{-3}$ | 1.54 $\times 10^{-3}$ | - |
| | AdCol | 24.46 | 16.75 | 7.71 | 0.0048 | - | - | - | - | 0.801 | 1.233 $\times 10^{-3}$ | 1.54 $\times 10^{-3}$ | 1.54 $\times 10^{-3}$ | - |
| | Calib. RNA | - | - | - | - | 25.96 | 18.57 | 7.39 | 0.00596 | 0.00596/0.00596 = 1 | - | | - | - |

FIG. 2

PATIENT CHARACTERISTICS

|  | N (%) |
|---|---|
| NO. OF PATIENTS | 56 (100) |
| SEX<br>    MALE<br>    FEMALE | <br>48 (85.7)<br>8 (14.3) |
| AGE, YEARS<br>    MEDIAN<br>    RANGE | <br>60.5<br>32–75 |
| ECOG PERFORMANCE STATUS<br>    0<br>    1<br>    2 | <br>13 (23.2)<br>35 (62.5)<br>8 (14.3) |
| WEIGHT LOSS | 21 (37.5) |
| STAGE<br>    IIIB<br>    IV | <br>16 (28.6)<br>40 (71.4) |
| PLEURAL EFFUSION | 11 (19.6) |
| HISTOPATHOLOGY<br>    ADENOCARCINOMA<br>    SQUAMOUS<br>    LARGE CELL<br>    UNDIFFERENTIATED | <br>30 (53.6)<br>20 (35.7)<br>4 (7.1)<br>2 (3.6) |
| RESPONSE<br>    COMPLETE RESPONSE<br>    PARTIAL RESPONSE<br>    STABLE DISEASE<br>    PROGRESSIVE DISEASE<br>    NOT EVALUABLE | <br>3 (5.4)<br>18 (32.1)<br>8 (14.3)<br>18 (32.1)<br>9 (16.1) |

FIG. 3

FACTORS ASSOCIATED WITH OVERALL SURVIVAL

| | MEDIAN SURVIVAL (WEEKS) | UNIVARIABLE ANALYSIS | | MULTIVARIABLE ANALYSIS | |
|---|---|---|---|---|---|
| | | LOG RANK STATISTIC | P VALUE | HAZARD RATIO (95% C.I.) | P VALUE |
| ERCC1 EXPRESSION LOW* HIGH* | 62 20 | 6.78 | 0.009 | 0.32 (0.14−0.71) | 0.005 |
| WEIGHT LOSS ABSENT PRESENT | 46 14 | 8.89 | <0.003 | 0.36 (0.17−0.75) | 0.007 |
| ECOG PERFORMANCE STATUS 0 1 2 | 61 31 5 | 10.29 | <0.005 | (0 VERSUS 1 OR 2) 0.26 (0.09−0.76) | 0.014 |

*CORRECTED RELATIVE ERCC1 EXPRESSION VALUES CATEGORIZED ACCORDING TO WHETHER LESS THAN THE CORRECTED RELATIVE ERCC1 THRESHOLD VALUE OF $6.7 \times 10^{-3}$ ("LOW EXPRESSION") OR GREATER THAN THE THRESHOLD ("HIGH EXPRESSION").

FIG. 4

SEQUENCE LISTING

```
<160> NUMBER OF SEQ ID NOS: 7
<210> SEQ ID NO 1
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 1
gggaatttgg cgacgtaatt c                                              21

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 2
gcggaggctg aggaacag                                                  18

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 3
cacaggtgct ctggcccagc acata                                          25

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 4
accaccacgg ccgagcgg                                                  18

<210> SEQ ID NO 5
<211> LENGTH: 18
<212> TYPE: DNA
```

```
<213> ORGANISM: Artificial Sequence
<220> FEATURE:
<223> OTHER INFORMATION: Oligonucleotide Primer

<400> SEQUENCE: 5
tgagcgcggc tacagctt                                                  18

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 6
tccttaatgt cacgcacgat                                                20

<210> SEQ ID NO 7
<211> LENGTH: 1097
<212> TYPE: DNA
<213> ORGANISM: Homo sapiens

<400> SEQUENCE: 7
aagtgctgcg agccctgggc cacgctggcc gtgctggcag tgggccgcct cgatccctct    60
gcagtctttc ccttgaggct ccaagaccag caggtgaggc ctcgcggcgc tgaaaccgtg   120
aggcccggac cacaggctcc agatggaccc tgggaaggac aaagaggggg tgccccagcc   180
ctcagggccg ccagcaagga agaaatttgt gatacccctc gacgaggatg aggtccctcc   240
tggagtggcc aagcccttat tccgatctac acagagcctt cccactgtgg cacctcggc    300 ccaggcggcc cctcagacct acgccgaata tgccatctca cagcctctgg aagggctgg    360 ggccacgtgc cccacagggt cagagcccct ggcaggagag acgcccaacc aggccctgaa   420
acccggggca aaatccaaca gcatcattgt gagccctcgg cagaggggca atcccgtact   480
gaagttcgtg cgcaacgtgc cctgggaatt tggcgacgta attcccgact atgtgctggg   540
ccagagcacc tgtgccctgt tcctcagcct ccgctaccac aacctgcacc cagactacat   600
ccatgggcgg ctgcagagcc tggggaagaa cttcgccttg cgggtcctgc ttgtccaggt   660
ggatgtgaaa gatccccagc aggccctcaa ggagctggct aagatgtgta tcctggccga   720
ctgcacattg atcctcgcct ggagccccga ggaagctggg cggtacctgg agacctacaa   780
ggcctatgag cagaaaccag cggacctcct gatggagaag ctagagcagg acttcgtctc   840
ccgggtgact gaatgtctga ccaccgtgaa gtcagtcaac aaaacggaca gtcagaccct   900
cctgaccaca tttggatctc tggaacagct catcgccgca tcaagagaag atctggcctt   960
atgcccaggc ctgggccctc agaaagcccg gaggctgttt gatgtcctgc acgagccctt  1020
cttgaaagta ccctgatgac cccagctgcc aaggaaaccc ccagtgtaat aataaatcgt  1080
cctcccaggc caggctc                                                 1097
```

METHOD OF DETERMINING A CHEMOTHERAPEUTIC REGIMEN BASED ON ERCC1 EXPRESSION

RELATED APPLICATIONS

This application is a continuation of U.S. patent application Ser. No. 09/988,784 filed Nov. 20, 2001, now U.S. Pat. No. 6,602,670, which is a continuation in part of U.S. patent application Ser. No. 09/877,095 filed Jun. 6, 2001, now U.S. Pat. No. 6,573,052, which is a continuation in part of U.S. patent application Ser. No. 09/796,491 filed Mar. 2, 2001, now U.S. Pat. No. 6,518,416, which claims priority to U.S. provisional patent applications 60/250,121 filed Dec. 1, 2000 and 60/250,470 filed Dec. 4, 2000 and these applications are hereby incorporated by reference herein.

FIELD OF THE INVENTION

The present invention relates to prognostic methods which are useful in medicine, particularly cancer chemotherapy. More particularly, the invention relates to assessment of tumor cell gene expression in a patient. The survival of patients treated with chemotherapeutic agents that target DNA, especially agents that damage DNA in the manner of platinating agents is assayed by examining the mRNA expressed from genes involved in DNA repair in humans.

BACKGROUND OF THE INVENTION

Cancer arises when a normal cell undergoes neoplastic transformation and becomes a malignant cell. Transformed (malignant) cells escape normal physiologic controls specifying cell phenotype and restraining cell proliferation. Transformed cells in an individual's body thus proliferate, forming a tumor. When a tumor is found, the clinical objective is to destroy malignant cells selectively while mitigating any harm caused to normal cells in the individual undergoing treatment.

Chemotherapy is based on the use of drugs that are selectively toxic (cytotoxic) to cancer cells. Several general classes of chemotherapeutic drugs have been developed, including drugs that interfere with nucleic acid synthesis, protein synthesis, and other vital metabolic processes. These generally are referred to as antimetabolite drugs. Other classes of chemotherapeutic drugs inflict damage on cellular DNA. Drugs of these classes generally are referred to as genotoxic. Susceptibility of an individual neoplasm to a desired chemotherapeutic drug or combination of drugs often, however, can be accurately assessed only after a trial period of treatment. The time invested in an unsuccessful trial period poses a significant risk in the clinical management of aggressive malignancies.

The repair of damage to cellular DNA is an important biological process carried out by a cell's enzymatic DNA repair machinery. Unrepaired lesions in a cell's genome can impede DNA replication, impair the replication fidelity of newly synthesized DNA and/or hinder the expression of genes needed for cell survival. Thus, genotoxic drugs generally are considered more toxic to actively dividing cells that engage in DNA synthesis than to quiescent, nondividing cells. Normal cells of many body tissues are quiescent and commit infrequently to re-enter the cell cycle and divide. Greater time between rounds of cell division generally is afforded for the repair of DNA damage in normal cells inflicted by chemotherapeutic genotoxins. As a result, some selectivity is achieved for the killing of cancer cells. Many treatment regimens reflect attempts to improve selectivity for cancer cells by coadministering chemotherapeutic drugs belonging to two or more of these general classes.

Because effective chemotherapy in solid tumors usually requires a combination of agents, the identification and quantification of determinants of resistance or sensitivity to each single drug has become an important tool to design individual combination chemotherapy.

Two widely used genotoxic anticancer drugs that have been shown to damage cellular DNA are cisplatin (DDP) and carboplatin. Cisplatin and/or carboplatin currently are used in the treatment of selected, diverse neoplasms of epithelial and mesenchymal origin, including carcinomas and sarcomas of the respiratory, gastrointestinal and reproductive tracts, of the central nervous system, and of squamous origin in the head and neck. Cisplatin in combination with other agents is currently preferred for the management of testicular carcinoma, and in many instances produces a lasting remission. (Loehrer et al., 1984,100 Ann. Int. Med. 704). Cisplatin (DDP) disrupts DNA structure through formation of intrastrand adducts. Resistance to platinum agents such as DDP has been attributed to enhanced tolerance to platinum adducts, decreased drug accumulation, or enhanced DNA repair. Although resistance to DDP is multifactoral, alterations in DNA repair mechanisms probably play a significant role. Excision repair of bulky DNA adducts, such as those formed by platinum agents, appears to be mediated by genes involved in DNA damage recognition and excision. Cleaver et al., Carcinogenesis 11:875–882 (1990); Hoeijmakers et al., Cancer Cells 2:311–320 (1990); Shivji et al., Cell 69:367–374 (1992). Indeed, cells carrying a genetic defect in one or more elements of the enzymatic DNA repair machinery are extremely sensitive to cisplatin. Fraval et al. (1978), 51 Mutat. Res. 121, Beck and Brubaker (1973), 116 J. Bacteriol 1247.

The excision repair cross-complementing (ERCC1) gene is essential in the repair of DNA adducts. The human ERCC1 gene has been cloned. Westerveld et al., Nature (London) 310:425–428 (1984); Tanaka et al., Nature 348: 73–76 (1990). Several studies using mutant human and hamster cell lines that are defective in this gene and studies in human tumor tissues indicate that the product encoded by ERCC1 is involved in the excision repair of platinum-DNA adducts. Dabholkar et al., J. Natl. Cancer Inst. 84:1512–1517 (1992); Dijt et al., Cancer Res. 48:6058–6062 (1988); Hansson et al., Nucleic Acids Res. 18: 35–40 (1990).

When transfected into DNA-repair deficient CHO cells, ERCC1 confers cellular resistance to cisplatin along with the ability to repair platinum-DNA adducts. Hansson et al., Nucleic Acids Res. 18: 35–40 (1990). Currently accepted models of excision repair suggest that the damage recognition/excision step is rate-limiting to the excision repair process.

The relative levels of expression of excision repair genes such as ERCC1 in malignant cells from cancer patients receiving platinum-based therapy has been examined. Dabholkar et al., J. Natl. Cancer Inst. 84:1512–1517 (1992). ERCC1 overexpression in gastric cancer patients has been reported to have a negative impact on tumor response and ultimate survival when treated with the chemotherapeutic regimen of cisplatin (DDP)/fluorouracil (Metzger, et al., J Clin Oncol 16: 309, 1998). Recent evidence indicates that gemcitabine (Gem) may modulate ERCC1 nucleotide excision repair (NER) activity. Thus, intratumoral levels of ERCC1 expression may be a major prognostic factor for determining whether or not DDP and GEM would be an effective therapeutic cancer patients.

Most pathological samples are routinely fixed and paraffin-embedded (FPE) to allow for histological analysis and subsequent archival storage. Thus, most biopsy tissue samples are not useful for analysis of gene expression because such studies require a high integrity of RNA so that an accurate measure of gene expression can be made. Currently, gene expression levels can be only qualitatively monitored in such fixed and embedded samples by using immunohistochemical staining to monitor protein expression levels.

Until now, quantitative gene expression studies including those of ERCC1 expression have been limited to reverse transcriptase polymerase chain reaction (RT-PCR) amplification of RNA from fresh or frozen tissue. U.S. Pat. No. 5,705,336 to Reed et al., discloses a method of quantifying ERCC1 mRNA from ovarian tumor tissue and determining whether that tissue will be sensitive to platinum-based chemotherapy. Reed et al., quanitfy ERCC1 mRNA from frozen ovarian tumor biopsies.

The use of frozen tissue by health care professionals as described in Reed et al., poses substantial inconveniences. Rapid biopsy delivery to avoid tissue and subsequent mRNA degradation is the primary concern when planning any RNA-based quantitative genetic marker assay. The health care professional performing the biopsy, must hastily deliver the tissue sample to a facility equipped to perform an RNA extraction protocol immediately upon tissue sample receipt. If no such facility is available, the clinician must promptly freeze the sample in order to prevent mRNA degradation. In order for the diagnostic facility to perform a useful RNA extraction protocol prior to tissue and RNA degradation, the tissue sample must remain frozen until it reaches the diagnostic facility, however far away that may be. Maintenance of frozen tissue integrity during transport using specialized couriers equipped with liquid nitrogen and dry ice, comes only at a great expense.

Routine biopsies generally comprise a heterogenous mix of stromal and tumorous tissue. Unlike with fresh or frozen tissue, FPE biopsy tissue samples are readily microdissected and separated into stromal and tumor tissue and therefore, offer andvantage over the use of fresh or frozen tissue. However, isolation of RNA from fixed tissue, and especially fixed and paraffin embedded tissue, results in highly degraded RNA, which is generally not applicable to gene expression studies.

A number of techniques exist for the purification of RNA from biological samples, but none is reliable for isolation of RNA from FPE samples. For example, Chomczynski (U.S. Pat. No. 5,346,994) describes a method for purifying RNA from tissues based on a liquid phase separation using phenol and guanidine isothiocyanate. A biological sample is homogenized in an aqueous solution of phenol and guanidine isothiocyanate and the homogenate thereafter mixed with chloroform. Following centrifugation, the homogenate separates into an organic phase, an interphase and an aqueous phase. Proteins are sequestered in the organic phase, DNA in the interphase, and RNA in the aqueous phase. RNA can be precipitated from the aqueous phase. Unfortunately, this method is not applicable to fixed and paraffin-embedded (FPE) tissue samples.

Other known techniques for isolating RNA typically utilize either guanidine salts or phenol extraction, as described for example in Sambrook, J. et al., (1989) at pp. 7.3–7.24, and in Ausubel, F. M. et al., (1994) at pp. 4.0.3–4.4.7. Again, none of the known methods provides reproducible quantitative results in the isolation of RNA from paraffin-embedded tissue samples.

Techniques for the isolation of RNA from paraffin-embedded tissues are thus particularly needed for the study of gene expression in tumor tissues, since expression levels of certain receptors or enzymes can be used to determine the likelihood of success of a particular treatment.

There is a need for a method of quantifying ERCC1 mRNA from paraffinized tissue in order to provide an early prognosis for proposed genotoxic cancer therapies. As a result, there has been a concerted yet unsuccessful effort in the art to obtain a quantification of ERCC1 expression in fixed and paraffmized (FPE) tissue. Accordingly, it is the object of the invention to provide a method for assessing ERCC1 levels in tissues fixed and paraffin-embedded (FPE) and prognosticate the probable resistance of a patient's tumor to treatment with DNA damaging agents, creating the type of lesions in DNA that are created by DNA platinating agents, by examination of the amount of ERCC1 mRNA in a patient's tumor cells and comparing it to a predetermined threshold expression level.

SUMMARY OF THE INVENTION

In one aspect of the invention there is provided a method for assessing levels of expression of ERCC1 mRNA obtained from fixed and paraffin-embedded (FPE) fixed and paraffin-embedded (FPE) tumor cells.

In another aspect of the invention there is provided a method of quantifying the amount of ERCC1 mRNA expression relative to an internal control from a fixed and paraffin-embedded (FPE) tissue sample. This method includes isolation of total mRNA from said sample and determining the quantity of ERCC1 mRNA relative to the quantity of an internal control gene's mRNA.

In an embodiment of this aspect of the invention, there are provided oligonucleotide primers having the sequence of ERCC1-504F (SEQ ID NO: 1) or ERCC1-574R (SEQ ID NO:2) and sequences substantially identical thereto. The invention also provides for oligonucleotide primers having a sequence that hybridizes to SEQ ID NO: 1 or SEQ ID NO:2 or their complements under stringent conditions.

In yet another aspect of the invention there is provided a method for determining a chemotherapeutic regimen for a patient, comprising isolating RNA from a fixed and paraffin-embedded (FPE) tumor sample; determining a gene expression level of ERCC1 in the sample; comparing the ERCC1 gene expression levels in the sample with a predeterimined threshold level for the ERCC1 gene; and determining a chemotherapeutic regimen based on results of the comparison of the ERCC1 gene expression level with the predetermined threshold level.

The invention further relates to a method of normalizing the uncorrected gene expression (UGE) of ERCC1 relative to an internal control gene in a tissue sample analyzed using TaqMan® technology to known ERCC1 expression levels relative to an internal control from samples analyzed by pre-TaqMan® technology.

BRIEF DESCRIPTION OF THE DRAWINGS

FIG. 4 is a table showing patients with Corrected ERCC1 expression levels below the threshold had a significantly longer median survival of 61.6 weeks (95% C.I. 42.4, 80.7 weeks) compared to 20.4 weeks (95% C.I. 6.9, 33.9 weeks) for patients with Corrected ERCC1 levels above the threshold. Adjusted for tumor stage, the log rank statistic for the association between low or high ERCC1 expression and overall survival was 3.97 and the P value was 0.046. The unadjusted log rank results are shown in this figure. Also shown are factors that were significantly associated with overall survival on univariable analysis using Kaplan Meier survival curves and the log rank test. These were the presence of pretreatment weight loss and the ECOG performance status. Patient age (P=0.18), sex (P=0.87), tumor stage (P=0.99), tumor cell type (P=0.63), and presence of pleural effusion (P=0.71) were not significant prognostic factors for overall survival. Corrected Relative ERCC1 Expression level, ECOG performance status, and weight loss remained significant prognostic factors for survival in the Cox proportional hazards regression model multivariable analysis. P values for a Cox regression model stratified on tumor stage were 0.038 for ERCC1, 0.017 for weight loss, and 0.02 for ECOG performance status (PS 0 versus 1 or 2).

DETAILED DESCRIPTION OF THE INVENTION

The present invention resides in part in the finding that the amount of ERCC1 mRNA in a tumor correlates with survival in patients treated with DNA platinating agents. Patients with tumors expressing high levels of ERCC1 mRNA are considered likely to be resistant to platinum-based chemotherapy and this have lower levels of survivability. Conversely, those patients whose tumors expressing low amounts of ERCC1 mRNA are likely to be sensitive to platinum-based chemotherapy and have greater levels of survivability. A patient's relative expression of tumor ERCC1 mRNA is judged by comparing it to a predetermined threshold expression level.

The invention relates to a method of quantifying the amount of ERCC1 mRNA expression in fixed and paraffin-embedded (FPE) tissue relative to gene expression of an internal control. The present inventors have developed oligonucleotide primers that allow accurate assessment of ERCC1 expression in tissues that have been fixed and embedded. The invention oligonucleotide primers, ERCC1-504F (SEQ ID NO: 1), ERCC1-574R (SEQ ID NO: 2), or oligonucleotide primers substantially identical thereto, preferably are used together with RNA extracted from fixed and paraffin embedded (FPE) tumor samples. This measurement of ERCC1 gene expression may then be used for prognosis of platinum-based chemotherapy.

This embodiment of the invention involves first, a method for reliable extraction of RNA from an FPE sample and second, determination of the content of ERCC1 mRNA in the sample by using a pair of oligonucleotide primers, preferably oligionucleotide primer pair ERCC1-504F (SEQ ID NO: 1) and ERCC1-574R (SEQ ID NO: 2), or oligonucleotides substantially identical thereto, for carrying out reverse transcriptase polymerase chain reaction. RNA is extracted from the FPE cells by any of the methods for mRNA isolation from such samples as described in U.S. patent application Ser. No. 09/469,338, filed Dec. 20, 1999, now U.S. Pat. No. 6,248,535, and is hereby incorporated by reference in its entirety.

The present method can be applied to any type of tissue from a patient. For examination of resistance of tumor tissue, it is preferable to examine the tumor tissue. In a preferred embodiment, a portion of normal tissue from the patient from which the tumor is obtained, is also examined. Patients whose normal tissues are expected to be resistant to platinum-based chemotherapeutic compounds, i.e., show a high level of ERCC1 gene expression, but whose tumors are expected to be sensitive to such compounds, i.e., show a low level of ERCC1 gene expression, may then be treated with higher amounts of the chemotherapeutic composition.

Patients showing a level of ERCC1 gene expression below the threshold level, may be treated with higher amounts of the chemotherapeutic composition because they are expected to have greater survivability than patients with tumors expressing a level of ERCC1 gene expression above the threshold level. Alternatively, the clinician may determine that patients with tumors expressing a level of ERCC1 gene expression above the threshold level may not derive any significant benefit from chemotherapy given their low expected survivability.

The methods of the present invention can be applied over a wide range of tumor types. This allows for the preparation of individual "tumor expression profiles" whereby expression levels of ERCC1 are determined in individual patient samples and response to various chemotherapeutics is predicted. Preferably, the methods of the invention are applied to solid tumors, most preferably Non-Small Cell Lung Cancer (NSCLC) tumors. For application of some embodiments of the invention to particular tumor types, it is preferable to confirm the relationship of ERCC1 gene expression levels to survivability by compiling a dataset that enables correlation of a particular ERCC1 expression and clinical resistance to platinum-based chemotherapy.

A "predetermined threshold level", as defined herein, is a corrected relative level of ERCC1 tumor expression above which it has been found that tumors are likely to be resistant to a platinum-based chemotherapeutic regimen. Tumor expression levels below this threshold level are likely to be found in tumors sensitive to platinum-based chemotherapeutic regimen. The range of corrected relative expression of ERCC1, expressed as a ratio of ERCC1: β-actin, among tumors responding to a platinum-based chemotherapeutic regimen is less than about $6.7 \times 10^{-3}$. Tumors that do not respond to a platinum-based chemotherapeutic regimen have relative expression of ERCC1: β-actin ratio above about 6.7×10⁻³. See Example 4.

Figure 1:
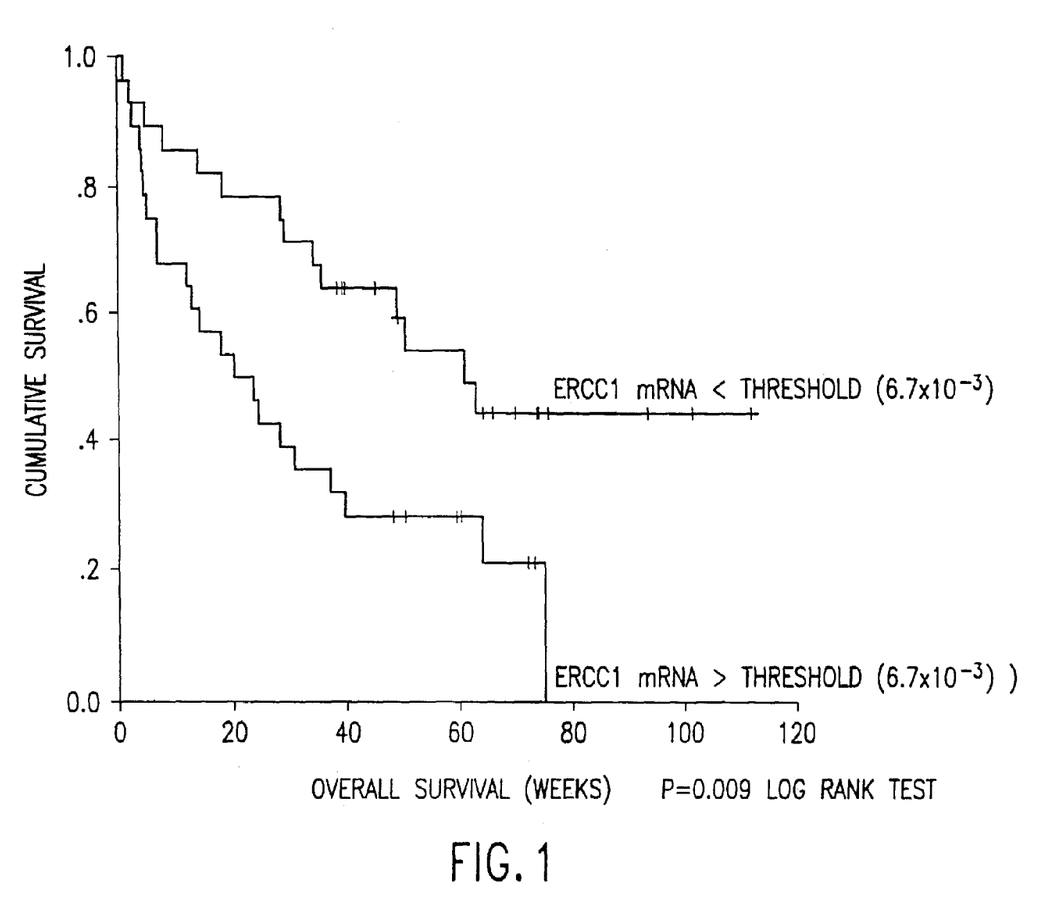
FIG. 1 is a graph showing the overall survival of patients receiving Cisplatin/Gem treatment vs. Corrected Relative ERCC1 Expression in NSCLC. Patient Corrected Relative ERCC1 Expression levels lower than the threshold of $6.7 \times 10^{-3}$ correlated with significantly better survival. While patient Corrected Relative ERCC1 Expression levels higher than the threshold of $6.7 \times 10^{-3}$ correlated with significantly worse survival. (P=0.009 Log rank test)

A "predetermined threshold level" is further defined as tumor corrected relative ERCC1 expression levels above which patients receiving a platinum-based chemotherapeutic regimen are likely to have low survivability. Tumor corrected relative ERCC1 expression levels below this threshold level in patients receiving a platinum-based chemotherapeutic regimen correlate to high patient survivability. The threshold corrected relative ERCC1 expression, expressed as a ratio of ERCC1: β-actin, is about 6.7×10⁻³. FIG. 1, see Example 4. However, the present invention is not limited to the use of β-actin as an internal control gene.

In performing the method of this embodiment of the present invention, tumor cells are preferably isolated from the patient. Solid or lymphoid tumors or portions thereof are surgically resected from the patient or obtained by routine biopsy. RNA isolated from frozen or fresh samples is extracted from the cells by any of the methods typical in the art, for example, Sambrook, Fischer and Maniatis, Molecular Cloning, a laboratory manual, (2nd ed.), Cold Spring Harbor Laboratory Press, New York, (1989). Preferably, care is taken to avoid degradation of the RNA during the extraction process.

However, tissue obtained from the patient after biopsy is often fixed, usually by formalin (formaldehyde) or gluteraldehyde, for example, or by alcohol immersion. Fixed biological samples are often dehydrated and embedded in paraffin or other solid supports known to those of skill in the art. Non-embedded, fixed tissue may also be used in the present methods. Such solid supports are envisioned to be removable with organic solvents for example, allowing for subsequent rehydration of preserved tissue.

RNA is extracted from the FPE cells by any of the methods as described in U.S. patent application Ser. No. 09/469,338, filed Dec. 20, 1999, now U.S. Pat. No. 6,248,535, which is hereby incorporated by reference in its entirety. Fixed and paraffin-embedded (FPE) tissue samples as described herein refers to storable or archival tissue samples. RNA may be isolated from an archival pathological sample or biopsy sample which is first deparaffinized. An exemplary deparaffinization method involves washing the paraffinized sample with an organic solvent, such as xylene, for example. Deparaffinized samples can be rehydrated with an aqueous solution of a lower alcohol. Suitable lower alcohols, for example include, methanol, ethanol, propanols, and butanols. Deparaffinized samples may be rehydrated with successive washes with lower alcoholic solutions of decreasing concentration, for example. Alternatively, the sample is simultaneously deparaffinized and rehydrated. RNA is then extracted from the sample.

For RNA extraction, the fixed or fixed and deparaffinized samples can be homogenized using mechanical, sonic or other means of homogenization. Rehydrated samples may be homogenized in a solution comprising a chaotropic agent, such as guanidinium thiocyanate (also sold as guanidinium isothiocyanate). Homogenized samples are heated to a temperature in the range of about 50 to about 100° C. in a chaotropic solution, which contains an effective amount of a chaotropic agent, such as a guanidinium compound. A preferred chaotropic agent is guanidinium thiocyanate.

An "effective concentration of chaotropic agent" is chosen such that at an RNA is purified from a paraffin-embedded sample in an amount of greater than about 10-fold that isolated in the absence of a chaotropic agent. Chaotropic agents include: guanidinium compounds, urea, formamide, potassium iodiode, potassium thiocyantate and similar compounds. The preferred chaotropic agent for the methods of the invention is a guanidinium compound, such as guanidinium isothiocyanate (also sold as guanidinium thiocyanate) and guanidinium hydrochloride. Many anionic counterions are useful, and one of skill in the art can prepare many guanidinium salts with such appropriate anions. The effective concentration of guanidinium solution used in the invention generally has a concentration in the range of about 1 to about 5M with a preferred value of about 4M. If RNA is already in solution, the guanidinium solution may be of higher concentration such that the final concentration achieved in the sample is in the range of about 1 to about 5M. The guanidinium solution also is preferably buffered to a pH of about 3 to about 6, more preferably about 4, with a suitable biochemical buffer such as Tris-Cl. The chaotropic solution may also contain reducing agents, such as dithiothreitol (DTT) and β-mercaptoethanol (BME). The chaotropic solution may also contain RNAse inhibitors.

Homogenized samples may be heated to a temperature in the range of about 50 to about 100° C. in a chaotropic solution, which contains an effective amount of a chaotropic agent, such as a guanidinium compound. A preferred chaotropic agent is guanidinium thiocyanate.

RNA is then recovered from the solution by, for example, phenol chloroform extraction, ion exchange chromatography or size-exclusion chromatography. RNA may then be further purified using the techniques of extraction, electrophoresis, chromatography, precipitation or other suitable techniques.

The quantification of ERCC1 mRNA from purified total mRNA from fresh, frozen or fixed is preferably carried out using reverse-transcriptase polymerase chain reaction (RT-PCR) methods common in the art, for example. Other methods of quantifying of ERCC1 mRNA include for example, the use of molecular beacons and other labeled probes useful in multiplex PCR. Additionally, the present invention envisages the quantification of ERCC1 mRNA via use of PCR-free systems employing, for example fluorescent labeled probes similar to those of the Invader® Assay (Third Wave Technologies, Inc.). Most preferably, quantification of ERCC1 cDNA and an internal control or house keeping gene (e.g. β-actin) is done sing a fluorescence based real-time detection method (ABI PRISM 7700 or 7900 Sequence Detection System [TaqMan®], Applied Biosystems, Foster City, Calif.) or similar system as described by Heid et al., (Genome Res 1996; 6:986–994) and Gibson et al. (Genome Res 1996; 6:995–1001). The output of the ABI 7700 (TaqMan® Instrument) is expressed in Ct's or "cycle thresholds". With the TaqMan® system, a highly expressed gene having a higher number of target molecules in a sample generates a signal with fewer PCR cycles (lower Ct) than a gene of lower relative expression with fewer target molecules (higher Ct).

As used herein, a "house keeping" gene or "internal control" is meant to include any constitutively or globally expressed gene whose presence enables an assessment of ERCC1 mRNA levels. Such an assessment comprises a determination of the overall constitutive level of gene transcription and a control for variations in RNA recovery. "House-keeping" genes or "internal controls" can include, but are not limited to the cyclophilin gene, β-actin gene, the transferrin receptor gene, GAPDH gene, and the like. Most preferably, the internal control gene is β-actin gene as described by Eads et al., Cancer Research 1999; 59:2302–2306.

A control for variations in RNA recovery requires the use of "calibrator RNA." The "calibrator RNA" is intended to be any available source of accurately pre-quantified control RNA. Preferably, Human Liver Total RNA (Stratagene, Cat. #735017) is used.

"Uncorrected Gene Expression (UGE)" as used herein refers to the numeric output of ERCC1 expression relative to an internal control gene generated by the TaqMan® instrument. The equation used to determine UGE is shown in Example 3, and illustrated with sample calculations in FIG. 2.

A further aspect of this invention provides a method to normalize uncorrected gene expression (UGE) values acquired from the TaqMan® instrument with "known relative gene expression" values derived from non-TaqMan® technology. Preferably, the known non-TaqMan® derived relative ERCC1: β-actin expression values are normalized with TaqMan® derived ERCC1 UGE values from a tissue sample.

Figure 2:
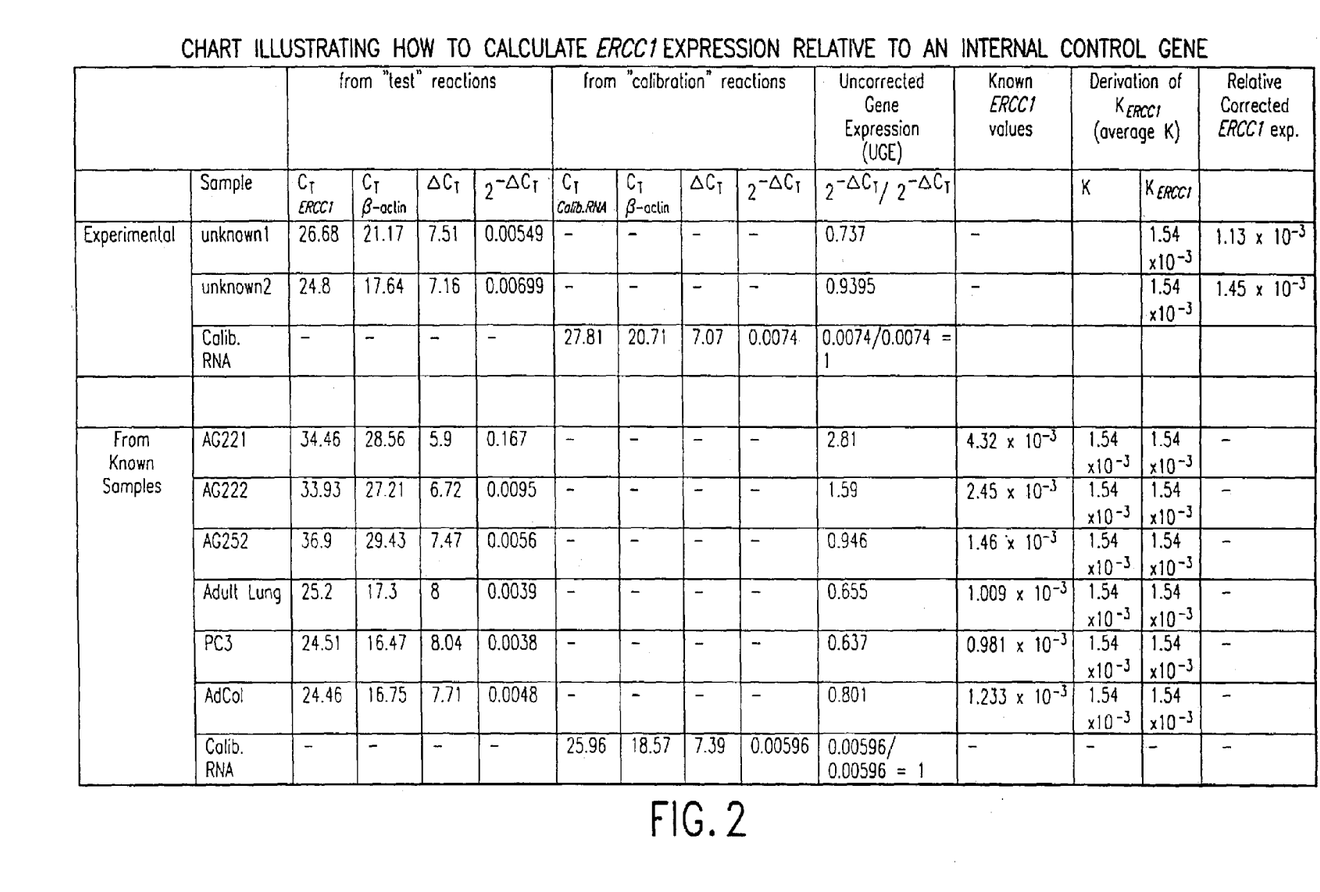
FIG. 2 is a chart illustrating how to calculate Corrected Relative ERCC1 expression relative to an internal control gene. The chart contains data obtained with two test samples, (unknowns 1 and 2), and illustrates how to determine the uncorrected gene expression data (UGE). The chart also illustrates how to normalize UGE generated by the TaqMan® instrument with known relative ERCC1 values determined by pre-TaqMan® technology. This is accomplished by multiplying UGE to a correction factor $K_{ERCC1}$. The internal control gene in the figure is β-actin and the calibrator RNA is Human Liver Total RNA (Stratagene, Cat. #735017).

"Corrected Relative ERCC1 Expression" as used herein refers to normalized ERCC1 expression whereby UGE is multiplied with a ERCC1 specific correction factor ($K_{ERCC1}$), resulting in a value that can be compared to a known range of ERCC1 expression levels relative to an internal control gene. Example 3 and FIG. 2 illustrate these calculations in detail. These numerical values allow the determination of whether or not the "Corrected Relative ERCC1 Expression" of a particular sample falls above or below the "predetermined threshold" level. The predetermined threshold level of Corrected Relative ERCC1 Expression to β-actin level is about $6.7 \times 10^{-3}$. $K_{ERCC1}$ specific for ERCC1, the internal control β-actin and calibrator Human Liver Total RNA (Stratagene, Cat. #735017), is $1.54 \times 10^{-3}$.

"Known relative gene expression" values are derived from previously analyzed tissue samples and are based on the ratio of the RT-PCR signal of a target gene to a constitutively expressed internal control gene (e.g. β-Actin, GAPDH, etc.). Preferably such tissue samples are formalin fixed and paraffin-embedded (FPE) samples and RNA is extracted from them according to the protocol described in Example 1 and in U.S. patent application Ser. No. 09/469, 338, filed Dec. 20, 1999, now U.S. Pat. No. 6,248,535, which is hereby incorporated by reference in its entirety. To quantify gene expression relative to an internal control standard quantitative RT-PCR technology known in the art is used. Pre-TaqMan® technology PCR reactions are run for a fixed number of cycles (i.e., 30) and endpoint values are reported for each sample. These values are then reported as a ratio of ERCC1 expression to β-actin expression. See U.S. Pat. No. 5,705,336 to Reed et al.

$K_{ERCC1}$ may be determined for an internal control gene other than β-actin and/or a calibrator RNA different than Human Liver Total RNA (Stratagene, Cat. #735017). To do so, one must calibrate both the internal control gene and the calibrator RNA to tissue samples for which ERCC1 expression levels relative to that particular internal control gene have already been determined (i.e., "known relative gene expression"). Preferably such tissue samples are formalin fixed and paraffin-embedded (FPE) samples and RNA is extracted from them according to the protocol described in Example 1 and in U.S. patent application Ser. No. 09/469, 338, filed Dec. 20, 1999, now U.S. Pat. No. 6,248,535, which is hereby incorporated by reference in its entirety. Such a determination can be made using standard pre-TaqMan®, quantitative RT-PCR techniques well known in the art. Upon such a determination, such samples have "known relative gene expression" levels of ERCC1 useful in the determining a new $K_{ERCC1}$ specific for the new internal control and/or calibrator RNA as described in Example 3.

The methods of the invention are applicable to a wide range of tissue and tumor types and so can be used for assessment of clinical treatment of a patient and as a diagnostic or prognostic tool for a range of cancers including breast, head and neck, lung, esophageal, colorectal, and others. In a preferred embodiment, the present methods are applied to prognosis of Non-Small Cell Lung Cancer (NSCLC).

Pre-chemotherapy treatment tumor biopsies are usually available only as fixed paraffin embedded (FPE) tissues, generally containing only a very small amount of heterogeneous tissue. Such FPE samples are readily amenable to microdissection, so that ERCC1 gene expression may be determined in tumor tissue uncontaminated with stromal tissue. Additionally, comparisons can be made between stromal and tumor tissue within a biopsy tissue sample, since such samples often contain both types of tissues.

Generally, any oligonucleotide pair that flanks a region of ERCC1 gene may be used to carry out the methods of the invention. Primers hybridizing under stringent conditions to a region of the ERCC1 gene for use in the present invention will amplify a product between 20–1000 base pairs, preferably 50–100 base pairs, most preferably less than 100 base pairs.

The invention provides specific oligonucleotide primers pairs and oligonucleotide primers substantially identical thereto, that allow particularly accurate assessment of ERCC1 expression in FPE tissues. Preferable are oligonucleotide primers, ERCC1-504F (SEQ ID NO: 1) and ERCC1 (SEQ ID NO: 2), (also referred to herein as the oligonucleotide primer pair ERCC1) and oligonucleotide primers substantially identical thereto. The oliogonucleotide primers ERCC1-504F (SEQ ID NO: 1) and ERCC1, (SEQ ID NO: 2) hybridize to the ERCC1 gene (SEQ ID NO: 7) under stringent conditions and have been shown to be particularly effective for measuring ERCC1 mRNA levels using RNA extracted from the FPE cells by any of the methods for mRNA isolation, for example as described Example 1 and in U.S. patent application Ser. No. 09/469, 338, filed Dec. 20, 1999, now U.S. Pat. No. 6,248,535, which is hereby incorporated by reference in its entirety.

"Substantially identical" in the nucleic acid context as used herein, means hybridization to a target under stringent conditions, and also that the nucleic acid segments, or their complementary strands, when compared, are the same when properly aligned, with the appropriate nucleotide insertions and deletions, in at least about 60% of the nucleotides, typically, at least about 70%, more typically, at least about 80%, usually, at least about 90%, and more usually, at least, about 95–98% of the nucleotides. Selective hybridization exists when the hybridization is more selective than total lack of specificity. See, Kanehisa, Nucleic Acids Res., 12:203–213 (1984).

This invention includes substantially identical oligonucleotides that hybridize under stringent conditions (as defined herein) to all or a portion of the oligonucleotide primer sequence of ERCC1-504F (SEQ ID NO: 1), its complement or ERCC1-574R (SEQ ID NO: 2), or its complement.

Under stringent hybridization conditions, only highly complementary, i.e., substantially similar nucleic acid sequences hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides.

The hybridizing portion of the nucleic acids is typically at least 10 (e.g., 15) nucleotides in length. The hybridizing portion of the hybridizing nucleic acid is at least about 80%, preferably at least about 95%, or most preferably about at least 98%, identical to the sequence of a portion or all of oligonucleotide primer ERCC1-504F (SEQ ID NO: 1), its complement or ERCC1-574R (SEQ ID NO: 2), or its complement.

Hybridization of the oligonucleotide primer to a nucleic acid sample under stringent conditions is defined below. Nucleic acid duplex or hybrid stability is expressed as a melting temperature ($T_m$), which is the temperature at which the probe dissociates from the target DNA. This melting temperature is used to define the required stringency conditions. If sequences are to be identified that are substantially identical to the probe, rather than identical, then it is useful to first establish the lowest temperature at which only homologous hybridization occurs with a particular concentration of salt (e.g. SSC or SSPE). Then assuming that 1% mismatching results in a 1° C. decrease in $T_m$, the temperature of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5×SSC/5× Denhart's solution/1.0% SDS, and washing in 0.2×SSC/0.1% SDS at room temperature. Moderately stringent conditions include washing in 3×SSC at 42° C. The parameters of salt concentration and temperature be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

Oligonucleotide primers disclosed herein are capable of allowing accurate assessment of ERCC1 gene expression in a fixed or fixed and paraffin embedded tissue, as well as frozen or fresh tissue. This is despite the fact that RNA derived from FPE samples is more fragmented relative to that of fresh or frozen tissue. Thus, the methods of the invention are suitable for use in assaying ERCC1 expression levels in FPE tissue where previously there existed no way to assay ERCC1 gene expression using fixed tissues.

From the measurement of the amount of ERCC1 mRNA that is expressed in the tumor, the skilled practitioner can make a prognosis concerning clinical resistance of a tumor to a particular genotoxin or the survivability of a patient receiving a particular genotoxin. A platinum-based chemotherapy or a chemotherapy inducing a similar type of DNA damage, is the preferable genotoxin.

Platinum-based chemotherapies cause a "bulky adduct" of the DNA, wherein the primary effect is to distort the three-dimensional conformation of the double helix. Such compounds are meant to be administered alone, or together with other chemotherapies such as gemcitabine (Gem) or 5-Fluorouracil (5-FU).

Platinum-based genotoxic chemotherapies comprises heavy metal coordination compounds which form covalent DNA adducts. Generally, these heavy metal compounds bind covalently to DNA to form, in pertinent part, cis-1,2-intrastrand dinucleotide adducts. Generally, this class is represented by cis-diamminedichloroplatinum (II) (cisplatin), and includes cis-diammine-(1,1-cyclobutanedicarboxylato) platinum(II) (carboplatin), cis-diammino-(1,2-cyclohexyl) dichloroplatinum(II), and cis-(1,2-ethylenediammine) dichloroplatinum(II). Platinum first agents include analogs or derivatives of any of the foregoing representative compounds.

Tumors currently manageable by platinum coordination compounds include testicular, endometrial, cervical, gastric, squamous cell, adrenocortical and small cell lung carcinomas along with medulloblastomas and neuroblastomas. Trans-Diamminedichloroplatinum (II) (trans-DDP) is clinically useless owing, it is thought, to the rapid repair of its DNA adducts. The use of trans-DDP as a chemotherapeutic agent herein likely would provide a compound with low toxicity in nonselected cells, and high relative toxicity in selected cells. In a preferred embodiment, the platinum compound is cisplatin.

Many compounds are commonly given with platinum-based chemotherapy agents. For example, BEP (bleomycin, etoposide, cisplatin) is used for testicular cancer, MVAC (methotrexate, vinblastine, doxorubicin, cisplatin) is used for bladder cancer, MVP (mitomycin C, vinblastine, cisplatin) is used for non-small cell lung cancer treatment. Many studies have documented interactions between platinum-containing agents. Therapeutic drug synergism, for example, has been reported for many drugs potentially included in a platinum based chemotherapy. A very short list of recent references for this include the following: Okamoto et al., Urology 2001; 57:188–192.; Tanaka et al., Anticancer Research 2001; 21:313–315; Slamon et al., Seminars in Oncology 2001; 28:13–19; Lidor et al., Journal of Clinical Investigation 1993; 92:2440–2447; Leopold et al., NCI Monographs 1987; 99–104; Ohta et al., Cancer Letters 2001; 162:39–48; van Moorsel et al., British Journal of Cancer 1999; 80:981–990.

Other genotoxic agents are those that form persistent genomic lesions and are preferred for use as chemotherapeutic agents in the clinical management of cancer. The rate of cellular repair of genotoxin-induced DNA damage, as well as the rate of cell growth via the cell division cycle, affects the outcome of genotoxin therapy. Unrepaired lesions in a cell's genome can impede DNA replication, impair the replication fidelity of newly synthesized DNA or hinder the expression of genes needed for cell survival. Thus, one determinant of a genotoxic agent's cytotoxicity (propensity for contributing to cell death) is the resistance of genomic lesions formed therefrom to cellular repair. Genotoxic agents that form persistent genomic lesions, e.g., lesions that remain in the genome at least until the cell commits to the cell cycle, generally are more effective cytotoxins than agents that form transient, easily repaired genomic lesions.

A general class of genotoxic compounds that are used for treating many cancers and that are affected by levels of ERCC1 expression are DNA alkylating agents and DNA intercalating agents. Psoralens are genotoxic compounds known to be useful in the photochemotherapeutic treatment of cutaneous diseases such as psoriasis, vitiligo, fungal infections and cutaneous T cell lymphoma. Harrison's Principles of Internal Medicine, Part 2 Cardinal Manifestations of Disease, Ch. 60 (12th ed. 1991). Another general class of genotoxic compounds, members of which can alkylate or intercalate into DNA, includes synthetically and naturally sourced antibiotics. Of particular interest herein are antineoplastic antibiotics, which include but are not limited to the following classes of compounds represented by: amsacrine; actinomycin A, C, D (alternatively known as dactinomycin) or F (alternatively KS4); azaserine; bleomycin; carminomycin (carubicin), daunomycin (daunorubicin), or 14-hydroxydaunomycin (adriamycin or doxorubicin); mitomycin A, B or C; mitoxantrone; plicamycin (mithramycin); and the like.

Still another general class of genotoxic agents that are commonly used and that alkylate DNA, are those that include the haloethylnitrosoureas, especially the chloroethylnitrosoureas. Representative members of this broad class include carmustine, chlorozotocin, fotemustine, lomustine, nimustine, ranimustine and streptozotocin. Haloethylnitrosourea first agents can be analogs or derivatives of any of the foregoing representative compounds.

Yet another general class of genotoxic agents, members of which alkylate DNA, includes the sulfur and nitrogen mustards. These compounds damage DNA primarily by forming covalent adducts at the N7 atom of guanine. Representative members of this broad class include chlorambucil, cyclophosphamide, ifosfamide, melphalan, mechloroethamine, novembicin, trofosfamide and the like. Oligonucleotides or analogs thereof that interact covalently or noncovalently with specific sequences in the genome of selected cells can also be used as genotoxic agents, if it is desired to select one or more predefined genomic targets as the locus of a genomic lesion.

Another class of agents, members of which alkylate DNA, include the ethylenimines and methylmelamines. These classes include altretamine (hexamethylmelamine), triethylenephosphoramide (TEPA), triethylenethiophosphoramide (ThioTEPA) and triethylenemelamine, for example.

Additional classes of DNA alkylating agents include the alkyl sulfonates, represented by busulfan; the azinidines, represented by benzodepa; and others, represented by, e.g., mitoguazone, mitoxantrone and procarbazine. Each of these classes includes analogs and derivatives of the respective representative compounds.

The invention being thus described, practice of the invention is illustrated by the experimental examples provided below. The skilled practitioner will realize that the materials and methods used in the illustrative examples can be modified in various ways. Such modifications are considered to fall within the scope of the present invention.

EXAMPLES

Example 1

RNA Isolation from FPE Tissue

RNA is extracted from paraffin-embedded tissue by the following general procedure.

A. Deparaffinization and Hydration of Sections:

(1) A portion of an approximately 10 μM section is placed in a 1.5 mL plastic centrifuge tube.

(2) 600 μL, of xylene are added and the mixture is shaken vigorously for about 10 minutes at room temperature (roughly 20 to 25° C.).

(3) The sample is centrifuged for about 7 minutes at room temperature at the maximum speed of the bench top centrifuge (about 10–20,000×g).

(4) Steps 2 and 3 are repeated until the majority of paraffin has been dissolved. Two or more times are normally required depending on the amount of paraffin included in the original sample portion.

(5) The xylene solution is removed by vigorously shaking with a lower alcohol, preferably with 100% ethanol (about 600 μL) for about 3 minutes.

(6) The tube is centrifuged for about 7 minutes as in step (3). The supernatant is decanted and discarded. The pellet becomes white.

(7) Steps 5 and 6 are repeated with successively more dilute ethanol solutions: first with about 95% ethanol, then with about 80% and finally with about 70% ethanol.

(8) The sample is centrifuged for 7 minutes at room temperature as in step (3). The supernatant is discarded and the pellet is allowed to dry at room temperature for about 5 minutes.

B. RNA Isolation with Phenol-Chloroform (1) 400 μL guanidine isothiocyanate solution including 0.5% sarcosine and 8 μL dithiothreitol is added.

(2) The sample is then homogenized with a tissue homogenizer (Ultra-Turrax, IKA-Works, Inc., Wilmington, N.C.) for about 2 to 3 minutes while gradually increasing the speed from low speed (speed 1) to high speed (speed 5).

(3) The sample is then heated at about 95° C. for about 5–20 minutes. It is preferable to pierce the cap of the tube containing the sample with a fine gauge needle before heating to 95° C. Alternatively, the cap may be affixed with a plastic clamp or with laboratory film.

(4) The sample is then extracted with 50 μL 2M sodium acetate at pH 4.0 and 600 μL of phenol/chloroform/isoamyl alcohol (10:1.93:0.036), prepared fresh by mixing 18 mL phenol with 3.6 mL of a 1:49 isoamyl alcohol:chloroform solution. The solution is shaken vigorously for about 10 seconds then cooled on ice for about 15 minutes.

(5) The solution is centrifuged for about 7 minutes at maximum speed. The upper (aqueous) phase is transferred to a new tube.

(6) The RNA is precipitated with about 10 μL glycogen and with 400 μL isopropanol for 30 minutes at −20° C.

(7) The RNA is pelleted by centrifugation for about 7 minutes in a benchtop centrifuge at maximum speed; the supernatant is decanted and discarded; and the pellet washed with approximately 500 μL of about 70 to 75% ethanol.

(8) The sample is centrifuged again for 7 minutes at maximum speed. The supernatant is decanted and the pellet air dried. The pellet is then dissolved in an appropriate buffer for further experiments (e.g., 50 pI. 5 mM Tris chloride, pH 8.0).

Example 2 mRNA Reverse Transcription and PCR

Reverse Transcription: RNA was isolated from microdissected or non-microdissected formalin fixed paraffin embedded (FPE) tissue as illustrated in Example 1 and as previously described in U.S. application Ser. No. 09/469,338 filed Dec. 20, 1999, which is hereby incorporated by reference in its entirety. After precipitation with ethanol and centrifugation, the RNA pellet was dissolved in 50 μl of 5 mM Tris/Cl at pH 8.0. M-MLV Reverse Transcriptase will extend an oligonucleotide primer hybridized to a single-stranded RNA or DNA template in the presence of deoxynucleotides, producing a complementary strand. The resulting RNA was reverse transcribed with random hexamers and M-MLV Reverse Transcriptase from Life Technologies. The reverse transcription was accomplished by mixing 25 μl of the RNA solution with 25.5 μl of "reverse transcription mix" (see below). The reaction was placed in a thermocycler for 8 min at 26° C. (for binding the random hexamers to RNA), 45 min at 42° C. (for the M-MLV reverse transcription enzymatic reaction) and 5 min at 95° C. (for heat inactivation of DNAse).

"Reverse transcription mix" consists of 10 ul 5× buffer (250 mM Tris-HCl, pH 8.3, 375 mM KCl, 15 mM MgCl2), 0.5 ul random hexamers (50 O.D. dissolved in 550 ul of 10 mM Tris-HCl pH 7.5) 5 ul 10 mM dNTPs (dATP, dGTP, dCTP and dTTP), 5 ul 0.1 M DTT, 1.25 ul BSA (3 mg/ml in 10 mM Tris-HCL, pH 7.5), 1.25 ul RNA Guard 24,800 U/ml (RNAse inhibitor) (Porcine #27-0816, Amersham Pharmacia) and 2.5 ul MMLV 200 U/ul (Life Tech Cat #28025-02).

Final concentrations of reaction components are: 50 mM Tris-HCl, pH 8.3, 75 mM KCl, 3 mM MgCl2, 1.0 mM dNTP, 1.0 mM DTT, 0.00375. mg/ml BSA, 0.62 U/ul RNA Guard and 10 U/ul MMLV.

PCR Quantification of mRNA expression. Quantification of ERCC1 cDNA and an internal control or house keeping gene (e.g., β-actin) cDNA was done using a fluorescence based real-time detection method (ABI PRISM 7700 or 7900 Sequence Detection System [TaqMan®], Applied Biosystems, Foster City, Calif.) as described by Heid et al., (Genome Res 1996; 6:986–994); Gibson et al., (Genome Res 1996; 6:995–1001). In brief, this method uses a dual labelled fluorogenic TaqMan® oligonucleotide probe, (ERCC1-530Tc (SEQ ID NO: 3), $T_m=70°$ C.), that anneals specifically within the forward and reverse primers. Laser stimulation within the capped wells containing the reaction mixture causes emission of a 3' quencher dye (TAMRA) until the probe is cleaved by the 5' to 3' nuclease activity of the DNA polymerase during PCR extension, causing release of a 5' reporter dye (6FAM). Production of an amplicon thus causes emission of a fluorescent signal that is detected by the TaqMan®'s CCD (charge-coupled device) detection camera, and the amount of signal produced at a threshold cycle within the purely exponential phase of the PCR reaction reflects the starting copy number of the sequence of interest. Comparison of the starting copy number of the sequence of interest with the starting copy number of the internal control gene provides a relative gene expression level. TaqMan® analyses yield values that are expressed as ratios between two absolute measurements (gene of interest/internal control gene).

The PCR reaction mixture consisted 0.5 μl of the reverse transcription reaction containing the cDNA prepared as described above 600 nM of each oligonucleoride primer (ERCC1-504F (SEQ ID NO:1), $T_m=59°$ C. and ERCC1-574R (SEQ ID NO: 2), $T_m=58°$ C.), 200 nM TaqMan® probe (SEQ ID NO:3), 5 U AmpliTaq Gold Polymerase, 200 μM each dATP, dCTP, dGTP, 400 μM dTTP, 5.5 mM $MgCl_2$, and 1× TaqMan® Buffer A containing a reference dye, to a final volume of less than or equal to 25 μl (all reagents Applied Biosystems, Foster City, Calif.). Cycling conditions were, 95° C. for 10 min, followed by 45 cycles at 95° C. for 15s and 60° C. for 1 min. Oligonucleotides used to quantify internal control gene β-Actin were β-Actin TaqMan® probe (SEQ ID NO: 4), β-Actin-592F (SEQ ID NO: 5) and β-Actin-651R (SEQ ID NO: 6).

The oligonucleotide primers ERCC1-504F (SEQ ID NO:1) and ERCC1-574R (SEQ ID NO: 2), used in the above described reaction will amplify a 71 bp product.

Example 3

Determining the Uncorrected Gene Expression (UGE) for ERCC1

Two pairs of parallel reactions are carried out, i.e., "test" reactions and the "calibration" reactions. The ERCC1 amplification reaction and the β-actin internal control amplification reaction are the test reactions. Separate ERCC1 and β-actin amplification reactions are performed on the calibrator RNA template and are referred to as the calibration reactions. The TaqMan® instrument will yield four different cycle threshold (Ct) values: $Ct_{ERCC1}$ and $Ct_{\beta\text{-}actin}$ from the test reactions and $Ct_{ERCC1}$ and $Ct_{\beta\text{-}actin}$ from the calibration reactions. The differences in Ct values for the two reactions are determined according to the following equation:

$$\Delta Ct_{test} = Ct_{ERCC1} - Ct_{\beta\text{-}actin} \text{ (From the "test" reaction)}$$

$$\Delta Ct_{calibrator} = Ct_{ERCC1} - Ct_{\beta\text{-}actin} \text{ (From the "calibration" reaction)}$$

Next the step involves raising the number 2 to the negative ΔCt, according to the following equations.

$$2^{-\Delta Ct_{test}} \text{ (From the "test" reaction)}$$

$$2^{-\Delta Ct_{calibrator}} \text{ (From the "calibration" reaction)}$$

In order to then obtain an uncorrected gene expression for ERCC1 from the TaqMan® instrument the following calculation is carried out:

Uncorrected gene expression (UGE) for $ERCC1 = 2^{-\Delta Ct_{test}} / 2^{-\Delta Ct_{calibrator}}$ Normalizing UGE with Known Relative ERCC1 Expression Levels The normalization calculation entails a multiplication of the UGE with a correction factor ($K_{ERCC1}$) specific to ERCC1 and a particular calibrator RNA. A correction factor $K_{ERCC1}$ can also be determined for any internal control gene and any accurately pre-quantified calibrator RNA. Preferably, the internal control gene β-actin and the accurately pre-quantified calibrator RNA Human Liver Total RNA (Stratagene, Cat. #735017), are used. Given these reagents correction factor $K_{ERCC1}$ equals $1.54 \times 10^{-3}$.

Normalization is accomplished using a modification of the ΔCt method described by Applied Biosystems, the TaqMan® manufacturer, in User Bulletin #2 and described above. To carry out this procedure, the UGE of 6 different test tissues was analyzed for ERCC1 expression using the TaqMan® methodology described above. The internal control gene β-actin and the calibrator RNA, Human Liver Total RNA (Stratagene, Cat. #735017) was used.

The known relative ERCC1 expression level of each sample AG221, AG222, AG252, Adult Lung, PC3, AdCol was divided by its corresponding TaqMan® derived UGE to yield an unaveraged correction factor K.

$$K_{unaveraged} = \text{Known Values}/UGE$$

Next, all of the K values are averaged to determine a single $K_{ERCC1}$ correction factor specific for ERCC1, Human Liver Total RNA (Stratagene, Cat. #735017) from calibrator RNA and β-actin.

Therefore, to determine the Corrected Relative ERCC1 Expression in an unknown tissue sample on a scale that is consistent with pre-TaqMan® ERCC1 expression studies, one merely multiplies the uncorrected gene expression data (UGE) derived from the TaqMan® apparatus with the $K_{ERCC1}$ specific correction factor, given the use of the same internal control gene and calibrator RNA.

Corrected Relative $ERCC1$ Expression $= UGE \times K_{ERCC1}$

A $K_{ERCC1}$ may be determined using any accurately pre-quantified calibrator RNA or internal control gene. Future sources of accurately pre-quantified RNA can be calibrated to samples with known relative ERCC1 expression levels as described in the method above or may now be calibrated against a previously calibrated calibrator RNA such as Human Liver Total RNA (Stratagene, Cat. #735017) described above.

For example, if a subsequent $K_{ERCC1}$ is determined for a different internal control gene and/or a different calibrator RNA, one must calibrate both the internal control gene and the calibrator RNA to tissue samples for which ERCC1 expression levels relative to that particular internal control gene have already been determined. Such a determination can be made using standard pre-TaqMan®, quantitative RT-PCR techniques well known in the art. The known expression levels for these samples will be divided by their corresponding UGE levels to determine a K for that sample. K values are then averaged depending on the number of known samples to determine a new $K_{ERCC1}$ specific to the different internal control gene and/or calibrator RNA.

Example 4

All patients were enrolled in the Cisplatin/Gemcitabine arm of a prospective multicenter three arm randomized trial (GEPC/98-02, Spanish Lung Cancer Group Phase III trial of Cisplatin/Gemcitabine (CG) versus Cisplatin/Gemcitabine/Vinorelbine (CGV) versus sequential doublets of Gemcitabine/Vinorelbine followed by Ifosfamide/Vinorelbine (GV/IV) in advanced NSCLC). All patients received Gem 1250 mg/m² days 1,8 plus CDDP 100 mg/m² day 1 every 3 weeks. Eligibility criteria for GEPC/98-02 were measurable stage IV (with brain metastases eligible if asymptomatic) or stage IIIB (malignant pleural and/or pericardial effusion and/or supraclavicular adenopathy) NSCLC and Eastern Cooperative Group (ECOG) performance score 0–2. All patients had chest x-ray and a computed tomography (CT) scan of the chest and upper abdomen before entry into the study and underwent repeat evaluations at least every 6 weeks. Tumor response was assessed according to WHO criteria as complete response, partial response, stable disease, and progressive disease. Tumors were reassessed during treatment with the same imaging methods used to establish the baseline tumor measurement.

Total mRNA was isolated from microdissected FPE pretreatment tumor samples, and Corrected Relative ERCC1 Expression was measured using quantitative RT-PCR as described in Examples 2 and 3. A method for mRNA isolation from such samples is described in Example 1 and in U.S. patent application Ser. No. 09/469,338, filed Dec. 20, 1999, and is hereby incorporated by reference in its entirety.

Statistical Analysis

The Mann-Whitney U test was used to test for significant associations between the continuous test variable Corrected Relative ERCC1 Expression and dichotomous variables (patient sex, age above and below the median age, presence of weight loss, presence of pleural effusion, tumor stage). The Kruskal-Wallis test was used to test for significant differences in Corrected Relative ERCC1 Expression within multiple groups (ECOG performance status, histopathology). Fisher's exact test was used for the analysis of categorical clinicopathological values including response and dichotomized Corrected Relative ERCC1 Expression values.

All patients were followed from first study treatment until death or until the data were censored. Kaplan-Meier survival curves and the log rank test were used to analyze univariate distributions for survival and disease-free survival. The maximal chi-square method of Miller and Siegmund (Biometrics 1982; 38:1011–1016 and Halpern (Biometrics 1982; 38:1017–1023) was adapted to determine which expression value best segregated patients into poor- and good prognosis subgroups (in terms of likelihood of surviving), with the log-rank test as the statistic used to measure the strength of the grouping. To determine a P value that would be interpreted as a measure of the strength of the association based on the maximal chi-square analysis, 1000 boot-strap-like simulations were used to estimate the distribution of the maximal chi-square statistics under the hypothesis of no association. (Biometrics 1982; 38:1017–1023) Cox's proportional hazards modeling of factors that were significant in univariate analysis was performed to identify which factors might have a significant influence on survival. SPSS version 10.0.5 software (SPSS Inc., Chicago Ill.) was used for all statistical analyses. All P values were two-sided.

Corrected Relative ERCC1 Expression Levels.

ERCC1 mRNA expression was detectable in all 56 samples analyzed. The median Corrected Relative ERCC1 Expression, relative to the expression of the internal control housekeeping gene β-actin, was $6.7 \times 10^{-3}$ (range $0.8 \times 10^{-3} - 24.6 \times 10^{-3}$). There were no significant associations between Corrected Relative ERCC1 Expression levels and any of the factors age (P=0.66), sex (P=0.18) presence of weight loss in the six months prior to randomization (P=0.74), tumor stage (IIIB versus IV, P=0.39), or presence of pleural effusion (P=0.25, all Mann-Whitney U test). There were also no significant differences between the Corrected Relative ERCC1 Expression levels among patients with different performance status grades (P=0.48, Kruskal-Wallis test) or different tumor cell types (all four tumor types, P=0.10, Kruskal-Wallis test), but Corrected Relative ERCC1 Expression levels were significantly higher in SCC tumors (median $8.6 \times 10^{-3}$) compared to adenocarcinomas (median $5.2 \times 10^{-3}$, P=0.015, Mann-Whitney test).

Response to Chemotherapy

Figure 3:
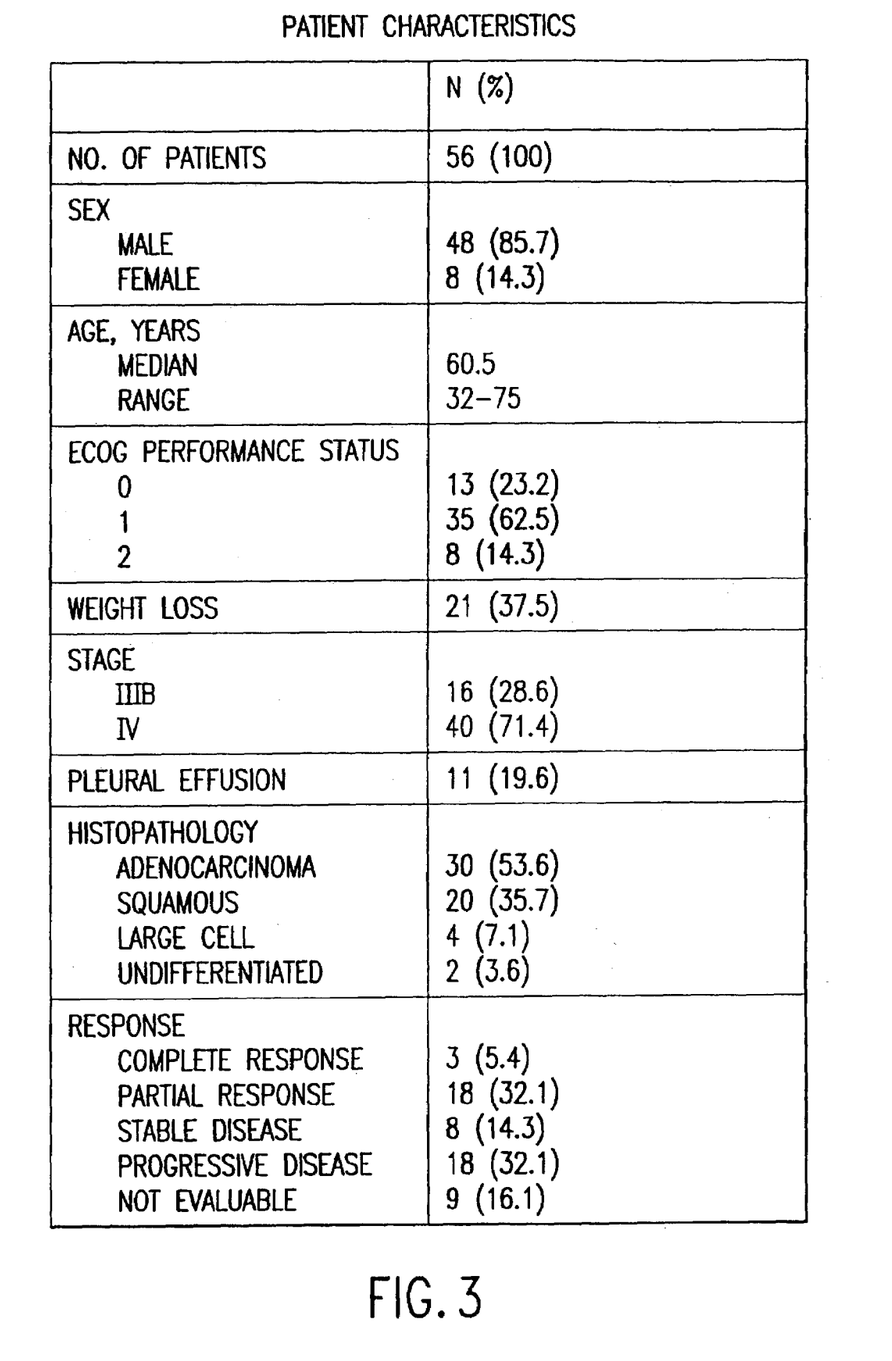
FIG. 3 is a table showing the demographic details of the 56 patients in the study, tumor stage and cell types. The median number of treatment cycles received was 3 (range 1–6). Fourteen patients (25%) had previously received chemotherapy, mostly (9 patients) taxane therapy alone or in combination with DDP or carboplatin. Three of the 56 patients had received radiotherapy and 5 patients had undergone surgical resection of the primary tumor.

The tumor response frequencies for the 47 patients who were evaluable for response are shown in FIG. 3. The overall response rate was 44.7%. The Corrected Relative ERCC1 Expression levels in the complete response and partial response i.e. "responding" tumors (median $4.3 \times 10^{-3}$, range $1.2 \times 10^{-3} - 24.6 \times 10^{-3}$) were not significantly different from the levels in the stable disease and progressive disease i.e. "non-responding" tumors (median $7.85 \times 10^{-3}$, range $0.8 \times 10^{-3} - 24.3 \times 10^{-3}$, P=0.31 Mann-Whitney test). There were also no significant differences between the proportion of responding and non-responding tumors with Corrected Relative ERCC1 Expression values greater and less than any ERCC1 level (all Fisher's exact test). The response rate in tumors with Corrected Relative ERCC1 Expression below the threshold value ("low" expression, 52% responders) was higher than for tumors with Corrected Relative ERCC1 Expression above the threshold value ("high" expression, 36.4% responders, Fisher's exact test, P=0.38).

Figure 4:
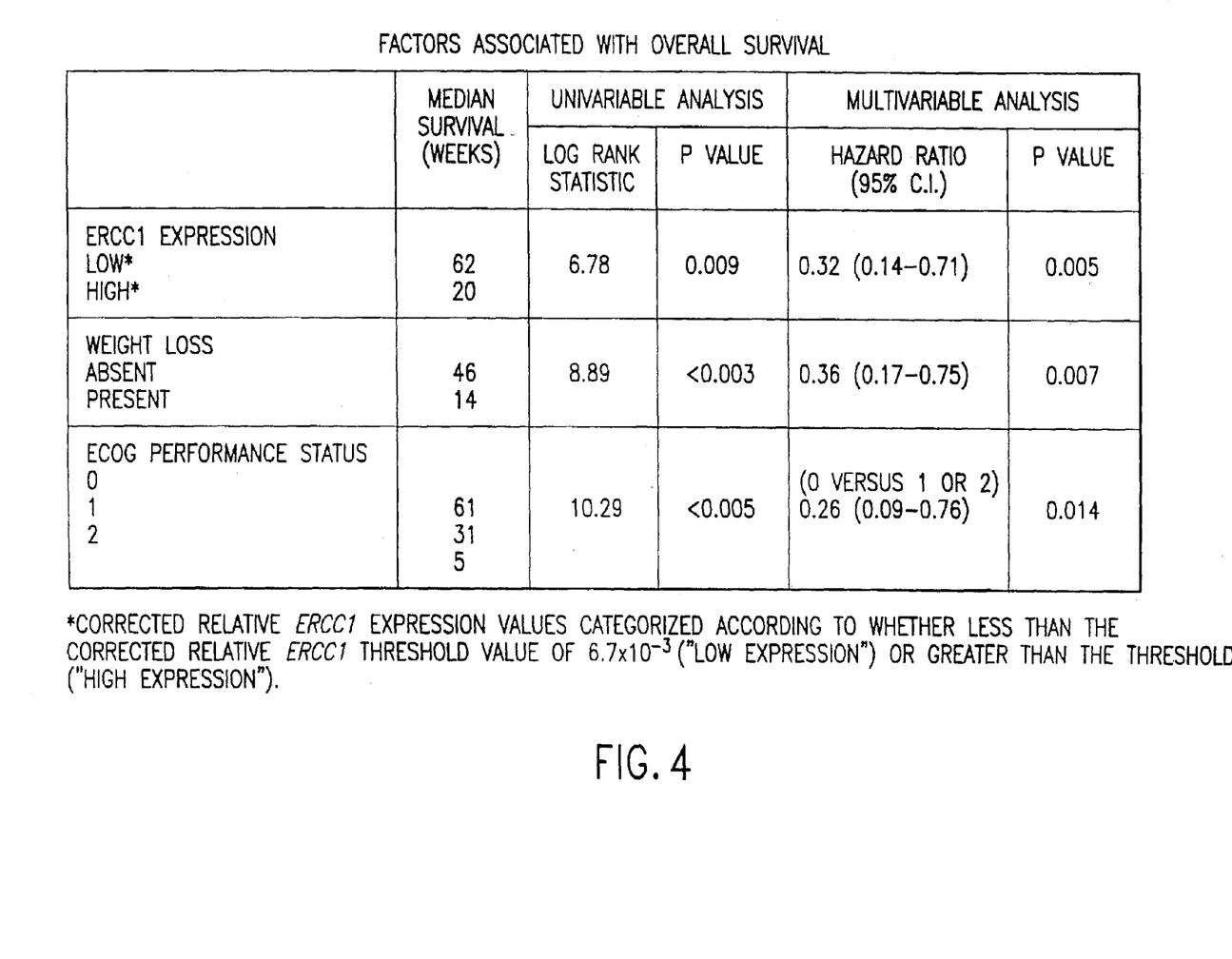

Association Between Patient Overall Survival and Corrected Relative ERCC1 Expression Levels The median overall survival time was 36.6 weeks (range 0–113.4 weeks) and the median time to progression was 24.4 weeks (range 0–102.9 weeks). Use of the log rank test and the maximal chi-square statistic to identify threshold Corrected Relative ERCC1 Expression levels that segregated patients into poor- and good-prognosis subgroups showed that the range of discriminatory values included the median value, which was therefore used as the threshold value for the survival analysis. Therefore, the threshold Corrected Relative ERCC1 Expression value was determined to be $6.7 \times 10^{-3}$ for NSCLC. FIG. 1 shows the Kaplan-Meier survival curve for patients with intratumoral Corrected Relative ERCC1 Expression levels above and below the threshold Corrected Relative ERCC1 Expression level. As shown in FIG. 4, patients with Corrected Relative ERCC1 Expression levels below the threshold value had a significantly longer median survival of 61.6 weeks (95% C.I. 42.4, 80.7 weeks) compared to 20.4 weeks (95% C.I. 6.9, 33.9 weeks) for patients with Corrected Relative ERCC1 Expression levels above the threshold value. Adjusted for tumor stage, the log rank statistic for the association between low or high Corrected Relative ERCC1 Expression and overall survival was 3.97 and the P value was 0.046. The unadjusted log rank results are shown in FIG. 4.

A separate Corrected Relative ERCC1 Expression threshold value of $5.8 \times 10^{-3}$ was tested because this value was shown in a previous study to be associated with overall survival for patients with gastric cancer. (Metzger et al., J Clin Oncol 1998; 16:309–316). Overall survival was significantly better for the group of NSCLC patients in this study with Corrected Relative ERCC1 Expression levels less than $5.8 \times 10^{-3}$ compared to those with ERCC1 levels less than $5.8 \times 10^{-3}$ (log rank statistic 6.37, P=0.011), although a higher $6.7 \times 10^{-3}$ Corrected Relative ERCC1 Expression threshold level is a more powerful discriminator.

Other factors that were significantly associated with overall survival on univariable analysis using Kaplan Meier survival curves and the log rank test were the presence of pretreatment weight loss and the ECOG performance status (Table 2). Patient age (P=0.18), sex (P=0.87), tumor stage (P=0.99), tumor cell type (P=0.63), and presence of pleural effusion (P=0.71) were not significant prognostic factors for overall survival. Corrected Relative ERCC1 Expression level, ECOG performance status, and weight loss remained significant prognostic factors for survival in the Cox proportional hazards regression model multivariable analysis (FIG. 4). P values for a Cox regression model stratified on tumor stage were 0.038 for ERCC1, 0.017 for weight loss, and 0.02 for ECOG performance status (PS 0 versus 1 or 2).

This study found an association between lower ERCC1 mRNA expression levels and improved survival after treatment with a platinum-based chemotherapeutic for patients with cancer.

The invention claimed is:

1. A method of treating a tumor with a platinum-based chemotherapeutic regimen comprising:
   (a) obtaining a tissue sample of the tumor and fixing the sample, to obtain a fixed tumor sample;
   (b) isolating mRNA from the fixed sample in the presence of an effective amount of a chaotrophic agent by first heating the tissue sample in a solution comprising an effective concentration of a chaotrophic compound to a temperature in the range of about 50 to about 100° C. for a time period of 5 to 120 minutes and recovering said mRNA from said chaotropic solution; and
   (c) subjecting the mRNA to amplification using a pair of oligonucleotide primers capable of amplifying a region of the Excision Repair Cross-Complementing 1 (ERCC1) gene, to obtain an amplified sample;
   (d) determining the amount of ERCC1 mRNA relative to the quantity of an internal control gene's mRNA; and (f) treating the tumor, wherein the treatment comprises providing a platinum-based chemotherapeutic regimen comprising a genotoxic agent when the determined gene expression level for ERCC1 gene is below a predetermined threshold value.

2. The method of claim 1 wherein the pair of oligonucleotide primers consists of SEQ lID NO: 1 or an oligonucleotide about 80% identical thereto and SEQ ID NO:2 or an oligonucleotide primer about 80% identical thereto.

3. The method of claim 1 wherein, the tumor is a non-small-cell lung cancer (NSCLC) tumor.

4. The claim 1 wherein, the genotoxic agent is gemcitabine, cisplatin or a combination thereof.

* * * * *